United States Patent
Bark et al.

(10) Patent No.: US 9,422,247 B2
(45) Date of Patent: Aug. 23, 2016

(54) FE(III) COMPLEX COMPOUNDS FOR THE TREATMENT AND PROPHYLAXIS OF IRON DEFICIENCY SYMPTOMS AND IRON DEFICIENCY ANEMIAS

(75) Inventors: Thomas Bark, Zürich (CH); Wilm Buhr, Constance (DE); Susanna Burckhardt, Zürich (CH); Michael Burgert, Friedrichshafen (DE); Camillo Canclini, St. Gallen (CH); Franz Dürrenberger, Dornach (CH); Felix Funk, Winterthur (CH); Peter Otto Geisser, St. Gallen (CH); Aris Kalogerakis, Winterthur (CH); Simona Mayer, Bühler (CH); Erik Philipp, Arbon (CH); Stefan Reim, Winterthur (CH); Diana Sieber, Abtwil (CH); Jörg Schmitt, Gaienhofen (DE); Katrin Schwarz, St. Gallen (CH)

(73) Assignee: Vifor (International) AG, St. Gallen (CH)

( * ) Notice: Subject to any disclaimer, the term of this patent is extended or adjusted under 35 U.S.C. 154(b) by 156 days.

(21) Appl. No.: 14/007,533

(22) PCT Filed: Mar. 28, 2012

(86) PCT No.: PCT/EP2012/055512
§ 371 (c)(1),
(2), (4) Date: Feb. 7, 2014

(87) PCT Pub. No.: WO2012/130882
PCT Pub. Date: Oct. 4, 2012

(65) Prior Publication Data
US 2014/0162994 A1    Jun. 12, 2014

(30) Foreign Application Priority Data

Mar. 29, 2011    (EP) ..................................... 11160151

(51) Int. Cl.
| | | |
|---|---|---|
| *A61K 31/555* | (2006.01) | |
| *A61K 45/06* | (2006.01) | |
| *C07D 239/34* | (2006.01) | |
| *C07D 239/70* | (2006.01) | |
| *C07D 239/80* | (2006.01) | |
| *C07D 239/47* | (2006.01) | |
| *A61K 31/513* | (2006.01) | |
| *A61K 33/26* | (2006.01) | |
| *C07D 239/46* | (2006.01) | |

(52) U.S. Cl.
CPC ............ *C07D 239/34* (2013.01); *A61K 31/513* (2013.01); *A61K 31/555* (2013.01); *A61K 33/26* (2013.01); *A61K 45/06* (2013.01); *C07D 239/46* (2013.01); *C07D 239/47* (2013.01); *C07D 239/70* (2013.01); *C07D 239/80* (2013.01)

(58) Field of Classification Search
CPC .. C07D 239/34; C07D 239/70; C07D 239/80; C07D 239/47; A61K 31/555; A61K 45/06
USPC .................................. 514/186, 184; 544/225
See application file for complete search history.

(56) References Cited

FOREIGN PATENT DOCUMENTS

EP            138420 A    4/1985

OTHER PUBLICATIONS

J. Ohkanda et al: "N-Hydroxyamide-Containing Heterocycles, Part 2. Synthesis and Iron (III) Complex-Forming Tendency of 1-Hydroxy-2(1H)-pyrimidinone and -pyrazinone," Bulletin of the Chemical Society of Japan, Jan. 1, 1993, pp. 841-847.

*Primary Examiner* — James O Wilson
*Assistant Examiner* — Ebenezer O Sackey
(74) *Attorney, Agent, or Firm* — Dilworth & Barrese, LLP

(57) ABSTRACT

The invention relates to iron(III) complex compounds and pharmaceutical compositions comprising them for the use as medicaments, in particular for the treatment and/or prophylaxis of iron deficiency symptoms and iron deficiency anemias.

12 Claims, No Drawings

# FE(III) COMPLEX COMPOUNDS FOR THE TREATMENT AND PROPHYLAXIS OF IRON DEFICIENCY SYMPTOMS AND IRON DEFICIENCY ANEMIAS

INTRODUCTION

The invention relates to iron(III)-pyrimidine-2-ol-1-oxide complex compounds and pharmaceutical compositions comprising them for the use as medicaments, in particular for the treatment and/or prophylaxis of iron deficiency symptoms and iron deficiency anemias.

BACKGROUND

Iron is an essential trace element for almost all organisms and is relevant in particular with respect to growth and the formation of blood. The balance of the iron metabolism is in this case primarily regulated on the level of iron recovery from hemoglobin of ageing erythrocytes and the duodenal absorption of dietary iron. The released iron is taken up via the intestine, in particular via specific transport systems (DMT-1, ferroportin, transferrin, transferrin receptors), transferred into the circulation and thereby conveyed to the appropriate tissues and organs.

In the human body, the element iron is of great importance for oxygen transport, oxygen uptake, cell functions such as mitochondrial electron transport, and ultimately for the entire energy metabolism.

On average, the human body contains 4 to 5 g iron, with it being present in enzymes, in hemoglobin and myoglobin, as well as depot or reserve iron in the form of ferritin and hemosiderin.

Approximately half of this iron, about 2 g, is present as heme iron, bound in the hemoglobin of the erythrocytes. Since these erythrocytes have only a limited lifespan (75-150 days), new ones have to be formed constantly and old ones eliminated (over 2 million erythrocytes are being formed per second). This high regenerative capacity is achieved by macrophages phagocytizing the ageing erythrocytes, lysing them and thus recycling the iron thus obtained for the iron metabolism. The amount of iron of about 25 mg required daily for erythropoiesis is thus provided for the main part.

The daily iron requirement of an adult human is between 0.5 to 1.5 mg per day, infants and women during pregnancy require 2 to 5 mg of iron per day. The daily iron loss, e.g. by desquamation of skin and epithelial cells, is low; increased iron loss occurs, for example, during menstrual hemorrhage in women. Generally, blood loss can significantly reduce the iron level since about 1 mg iron is lost per 2 ml blood. In a healthy human adult, the normal daily loss of iron of about 1 mg is usually replaced via the daily food intake. The iron level is regulated by absorption, with the absorption rate of the iron present in food being between 6 and 12%; in the case of iron deficiency, the absorption rate is up to 25%. The absorption rate is regulated by the organism depending on the iron requirement and the size of the iron store. In the process, the human organism utilizes both divalent as well as trivalent iron ions. Usually, iron(III) compounds are dissolved in the stomach at a sufficiently acid pH value and thus made available for absorption. The absorption of the iron is carried out in the upper small intestine by mucosal cells. In the process, trivalent non-heme iron is first reduced in the intestinal cell membrane to Fe(II) for absorption, for example by ferric reductase (membrane-bound duodenal cytochrome b), so that it can then be transported into the intestinal cells by means of the transport protein DMT1 (divalent metal transporter 1). In contrast, heme iron enters the enterocytes through the cell membrane without any change. In the enterocytes, iron is either stored in ferritin as depot iron, or discharged into the blood by the transport protein ferroportin. Hepcidin plays a central role in this process because it is the most important regulating factor of iron uptake. The divalent iron transported into the blood by ferroportin is converted into trivalent iron by oxidases (ceruloplasmin, hephaestin), the trivalent iron then being transported to the relevant places in the organism by transferrin (see for example "Balancing acts: molecular control of mammalian iron metabolism". M. W. Hentze, *Cell* 117, 2004, 285-297.)

Mammalian organisms are unable to actively discharge iron. The iron metabolism is substantially controlled by hepcidin via the cellular release of iron from macrophages, hepatocytes and enterocytes.

In pathological cases, a reduced serum iron level leads to a reduced hemoglobin level, reduced erythrocyte production and thus to anemia.

External symptoms of anemias include fatigue, pallor as well as reduced capacity for concentration. The clinical symptoms of an anemia include low serum iron levels (hypoferremia), low hemoglobin levels, low hematocrit levels as well as a reduced number of erythrocytes, reduced reticulocytes and elevated levels of soluble transferrin receptors.

Iron deficiency symptoms or iron anemias are treated by supplying iron. In this case, iron substitution takes place either orally or by intravenous iron administration. Furthermore, in order to boost erythrocyte formation, erythropoietin and other erythropoiesis-stimulating substances can also be used in the treatment of anemias.

Anemia can often be traced back to malnutrition or low-iron diets or imbalanced nutritional habits low in iron. Moreover, anemias occur due to reduced or poor iron absorption, for example because of gastroectomies or diseases such as Crohn's disease. Moreover, iron deficiency can occur as a consequence of increased blood loss, such as because of an injury, strong menstrual bleeding or blood donation. Furthermore, an increased iron requirement in the growth phase of adolescents and children as well as in pregnant women is known. Since iron deficiency not only leads to a reduced erythrocyte formation, but thereby also to a poor oxygen supply of the organism, which can lead to the above-mentioned symptoms such as fatigue, pallor, reduced powers of concentration, and especially in adolescents, to long-term negative effects on cognitive development, a highly effective and well tolerated therapy is of particular interest.

Through using the Fe(III) complex compounds according to the invention, there is the possibility of treating iron deficiency symptoms and iron deficiency anemias effectively by oral application without having to accept the large potential for side effects of the classical preparations, the Fe(II) iron salts, such as $FeSO_4$, which is caused by oxidative stress. Poor compliance, which often is the reason for the deficient elimination of the iron deficiency condition, is thus avoided.

PRIOR ART

A multitude of iron complexes for the treatment of iron deficiency conditions is known from the prior art.

A very large proportion of these complex compounds consists of polymer structures. Most of these complex compounds are iron-polysaccharide complex compounds (WO20081455586, WO2007062546, WO20040437865, US2003236224, EP150085). It is precisely from this area that there are medicaments available on the market (such as Maltofer, Venofer, Ferinject, Dexferrum, Ferumoxytol).

Another large portion of the group of the polymer complex compounds is comprised of the iron-peptide complex compounds (CN101481404, EP939083, JP02083400).

There are also Fe complex compounds described in the literature that are structurally derived from macromolecules such as hemoglobin, chlorophyll, curcumin and heparin (U.S. Pat. No. 474,670, CN1687089, Biometals, 2009, 22, 701-710).

Moreover, low-molecular Fe complex compounds are also described in the literature. A large number of these Fe complex compounds comprises carboxylic acid and amino acids as ligands. In this case, the focus is on aspartate (US2009035385) and citrate (EP308362) as ligands. Fe complex compounds containing derivatized phenylalanine groups as ligands are also described in this context (ES2044777).

Hydroxypyrone and hydroxypyridone Fe complex compounds are also described in the literature (EP159194, EP138420, EP107458). The corresponding 5-ring systems, the hydroxyfuranone Fe complex compounds, are also described in analogy thereto (WO2006037449). In particular, the hydroxypyridone Fe complex compounds, however, have comparatively low water solubility, making them less suitable, especially for oral administration. Furthermore the hydroxypyridone Fe complex compounds have comparatively low iron utilization.

Moreover, iron-cyclopentadienyl complex compounds are also described in the literature (GB842637).

Furthermore, 1-hydroxy-4,6-dimethyl-2(1H)-pyrimidone are described in the literature as Fe(III) ligands (Bull. Chem. Soc. Jpn., 66, 841-841 (1993), and as a possible structure of a corresponding iron(III) complex the following structure is specified:

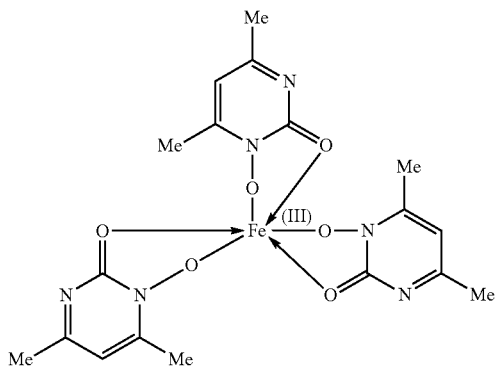

(see also "Reviews On Heteroatom Chemistry", vol. 18, 1998, pages 87 to 118 from the same authors). A characterization of this complex was only carried out in solution. A solid form of this complex is not disclosed. Furthermore, the iron complex compounds are not proposed or used as medicaments, such as especially for the treatment of iron deficiency symptoms. The same authors suggest only the use of hexadentate 1-hydroxy-1H-pyrimidine-2-one compounds as iron sequestering agents for treatment of iron overload conditions such as thalassemia (J. Org. Chem. 1997, 62, 3618-3624). By the administration of hydroxy-pyrimidinone compounds to the body for the treatment of thalassemia iron might be removed—so no iron will be supplied—as in the treatment of iron deficiency anemia by administration of iron complex compounds in accordance with the present invention.

J. Am. Chem. Soc. 1985, 107, 6540-6546 describes tetradentate 1-hydroxy-1H-pyridine-2-one compounds as ligands and a binuclear iron complex compound therewith. The possibility to use the ligands for iron sequestering is mentioned, too. Similarly, Inorganica Chimica Acta, 135 (1987) 145-150 discloses the use of 1-hydroxy-1H-pyridine-2-ones as agents for masking iron.

Iron salts (e.g. iron(II) sulfate, iron(II) fumarate, iron(III) chloride, iron(II) aspartate, iron(II) succinate) are another important constituent for the treatment of iron deficiency symptoms and iron deficiency anemias.

These iron salts are very problematic in that, in part, they are highly incompatible (up to 50%) in the form of nausea, vomiting, diarrhea and also obstipation and cramps. Moreover, free iron(II) ions which catalyze the formation (inter alia Fenton reaction) of reactive oxygen species (ROS) occur during the use of these iron(II) salts. These ROS cause damage to DNA, lipids, proteins and carbohydrates which has far-reaching effects in cells, tissue and organs. This complex of problems is known and, in the literature, is largely considered the cause for the high incompatibility and referred to as oxidative stress.

Therefore, iron(III)-1-hydroxy-1H-pyrimidine-2-one or pyrimidine-2-ol-1-oxide complex compounds, respectively, have not been described in the prior art neither as a medicament nor in particular for the use in the treatment and/or for prophylaxis of iron deficiency symptoms and iron deficiency anemia so far.

OBJECT

The object of the present invention lay in developing new therapeutically effective compounds that can be used for an effective therapy for the preferably oral treatment of iron deficiency symptoms and iron deficiency anemias. In this case, these iron complexes were supposed to exhibit significantly fewer side effects than the classically used Fe(II) salts. Furthermore, these iron complexes, in contrast to the known polymeric iron complex compounds, were, if possible, supposed to have a defined structure (stoichiometry) and be preparable by simple synthesis processes. Finally, the iron complex compounds should have a very low toxicity and can be therefore administered in very high dosages. This goal was achieved by the development of novel Fe(III) complex compounds.

Furthermore, the novel iron complexes were supposed to be designed such that they are taken up into the intestinal cells directly via the membrane in order thus to release their complex-bound iron directly to the ferritin or the transferrin or to reach the bloodstream directly as an intact complex. Because of their properties, these new complexes are supposed to virtually not lead to the occurrence of high concentrations of free iron ions. For it is precisely the free iron ions that lead to the occurrence of ROS which are ultimately responsible for the side effects that occur.

In order to be able to meet these requirements, the inventors developed new Fe(III) complex compounds with a molecular weight that is not too large, medium lipophila and an optimal complex stability.

DESCRIPTION OF THE INVENTION

The inventors surprisingly found that Fe(III) complex compounds with pyrimidine-2-ol-1-oxide ligands were particularly suitable for the above-described requirements. It was possible to demonstrate that these Fe complex compounds exhibited a high iron uptake, whereby a quick therapeutic success in the treatment of iron deficiency anemia could be achieved. Especially in comparison to iron salts, the complex compounds according to the invention exhibited a faster and higher utilization. Furthermore, these new systems have significantly reduced side effects than the classically used iron salts since there is no noteworthy occurrence of free iron irons in this case. The complex compounds according to the invention exhibit almost no oxidative stress since there is no formation of free radicals. Thus, significantly fewer side effects occur in the case of these complex compounds than in the case of the Fe salts known from the prior art. The complex compounds exhibit good stability at various pH value ranges. Furthermore, the iron complex compounds have a very low toxicity and can therefore be administered in high dosages without side effects. Finally the complex compounds can be prepared well and are optimally suitable for the formulation of medicaments, in particular for oral administration.

Thus, the subject matter of the invention are iron(III)-pyrimidine-2-ol-1-oxide complex compounds or their pharmaceutically acceptable salts for use as medicaments or synonymous for use in a method for therapeutic treatment of the human body, respectively.

The iron(III)-pyrimidine-2-ol-1-oxide complex compounds as used in accordance with the present invention particularly include such compounds with comprise the following structural element:

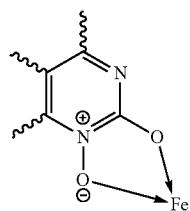

wherein ～ respectively is a substituent saturating the free valence and the arrows respectively represent coordinate bonds to the iron atom.

Thus, the terms

"pyrimidine-2-ol-1-oxide",

"pyrimidine-2-ol-1-oxide compounds" or

"pyrimidine-2-ol-1-oxide-" ligands according to the invention include the corresponding hydroxy starting compounds

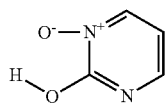

as well as the corresponding deprotonated ligands

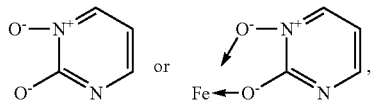

respectively,
which are present in the corresponding iron(III) complex compounds.

Furthermore, according to the invention the aforementioned terms do not only comprise the respective base body:

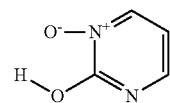

or the ligand compound resulting from deprotonating the underlying hydroxy compound

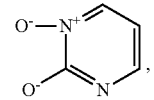

respectively but as well their representatives substituted on the pyrimidine rings, resulting from the replacement of one or more hydrogen atoms on the pyrimidine ring by other substituents. Accordingly, in context with the present invention the aforementioned terms refer to the entire class of "pyrimidine-2-ol-1-oxide" compounds and the deprotonated ligands, including their representatives substituted on the pyrimidine ring.

Formally, a (deprotonated) pyrimidine-2-ol-1-oxide ligand according to the present invention carries a negative charge. This means, that in the case of three ligands per iron atom, the iron atom formally has the oxidation state +3. It is clear to the person skilled in the art that the shown formulas represent only one possible mesomeric formula and that there are several mesomeric formulas and that delocalisation of the electrons in the ligands or in the iron complex compound may be present, respectively, as shown hereinafter schematically.

In the iron(III) pyrimidine-2-ol-1-oxide complex compounds according to the invention, the coordination number of the iron atoms is generally six (6), with a coordinating atoms generally being arranged octahedrally.

Furthermore, mono- or polynuclear iron(III) pyrimidine-2-ol-1-oxide complex compounds in which one or more (such as 2, 3 or 4) iron atoms are present are also comprised according to the invention.

Generally, 1-4 iron atoms and 2-10 ligands can be present in the iron(III) pyrimidine-2-ol-1-oxide complex compounds. Mononuclear iron(III) pyrimidine-2-ol-1-oxide complex compounds with at least one preferably tri-, preferably bidentate pyrimidine-2-ol-1-oxide ligands are preferred. Mononuclear iron(III) pyrimidine-2-ol-1-oxide complex compounds with one (1) central iron atom and three (3) pyrimidine-2-ol-1-oxide ligands are particularly preferred.

The iron(III) pyrimidine-2-ol-1-oxide complex compounds are generally present in neutral form. However, salt like iron(III) pyrimidine-2-ol-1-oxide complex compounds are also included, in which the complex has a positive or negative charge which is compensated, in particular, by pharmacologically compatible, substantially non-coordinating anions (such as, in particular, halogenides, such as chloride) or cations (such as, in particular, alkaline or alkaline-earth metal ions).

The iron(III) pyrimidine-2-ol-1-oxide complex compounds according to the invention particularly include complex compounds, comprising at least one, preferably a bidentate pyrimidine-2-ol-1-oxide ligand of the formula

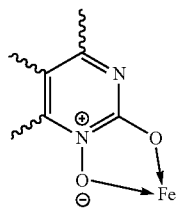

wherein ⁓ respectively is a substituent saturating the free valence of the ligands, which can, as shown above, bond to one or even two different iron atoms in the sense of bridging.

Iron(III) pyrimidine-2-ol-1-oxide complex compounds are preferred which exclusively comprise preferably bidentate pyrimidine-2-ol-1-oxide ligands which may be the same or different. Furthermore, iron(III) pyrimidine-2-ol-1-oxide complex compounds are particularly preferred which exclusively comprise the same pyrimidine-2-ol-1-oxide ligands and very particularly preferred are tris(pyrimidine-2-ol-1-oxide) iron(III) compounds.

Preferably, the molecular weight of the inventive iron (III)-pyrimidin-2-ol 1-oxide-complex compounds is less than 1000 g/mol, more preferably less than 850 g/mol, still more preferably less than 700 g/mol (each determined from the structural formula).

In a particularly preferred embodiment the iron(III) complex compounds according to the present invention comprise at least one, preferably three same or different, preferably same ligands of the formula (I):

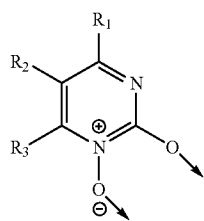

(I)

wherein
the arrows respectively represent a coordinate bond to one or different iron atoms, and $R_1$, $R_2$, $R_3$ may be the same or different and are selected from the group consisting of:
hydrogen,
optionally substituted alkyl,
halogen,
optionally substituted alkoxy,
optionally substituted aryl,
optionally substituted alkoxycarbonyl,
optionally substituted amino, and
optionally substituted aminocarbonyl or $R_1$ and $R_2$ or $R_2$ and $R_3$ together with the carbon atoms to which they are bonded, form an optionally substituted saturated or unsaturated 5- or 6-membered ring, which may optionally contain one or more heteroatoms, or pharmaceutically acceptable salts thereof.

The above-mentioned ring formation of the substituents $R_1$ and $R_2$ or $R_2$ and $R_3$ is schematically shown in the following formulas:

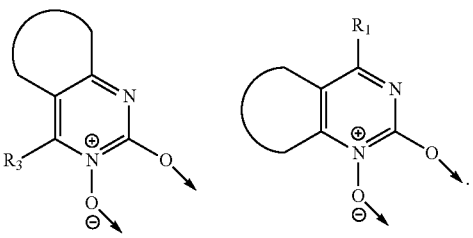

A preferred embodiment of the present invention relates to these iron(III) complex compounds containing at least one ligand of the formula (I):

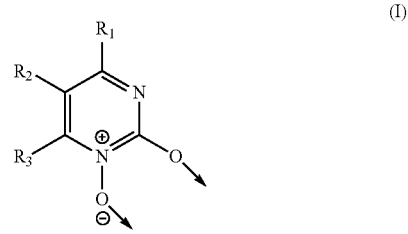

(I)

wherein
the arrows respectively represent a coordinate bond to one or different iron atoms, and $R_1$, $R_2$, $R_3$ may be the same or different and are selected from the group consisting of:
hydrogen,
optionally substituted alkyl,
halogen,
optionally substituted alkoxy,
optionally substituted aryl,
optionally substituted alkoxycarbonyl, and
optionally substituted aminocarbonyl or $R_1$ and $R_2$ or $R_2$ and $R_3$ together with the carbon atoms to which they are bonded, form an optionally substituted saturated or unsaturated 5- or 6-membered ring, which may optionally contain one or more heteroatoms, or pharmaceutically acceptable salts thereof.

A preferred embodiment of the present invention relates to these iron(III) complex compounds containing at least one ligand of the formula (I):

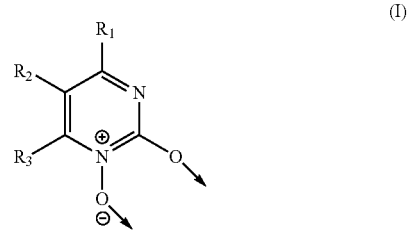

(I)

wherein the arrows respectively represent a coordinate bond to one or different iron atoms, and $R_1$, $R_2$, $R_3$ may be the same or different and are selected from the group consisting of:
hydrogen
optionally substituted alkyl, and
halogen.

Within the overall context of the invention, optionally substituted alkyl, in particular for the substituents $R_1$ to $R_3$, preferably includes:
straight-chained or branched alkyl with 1 to 8, preferably 1 to 6 carbon atoms, cycloalkyl with 3 to 8, preferably 5 or 6 carbon atoms, or alkyl with 1 to 4 carbon atoms, which is substituted with cycloalkyl, wherein these alkyl groups can be optionally substituted.

The above mentioned alkyl groups can be unsubstituted or substituted, preferably with 1 to 3 substituents. These substituents at the alkyl groups are preferably selected from the group consisting of: hydroxy, optionally substituted aryl, in particular as defined below, optionally substituted heteroaryl, in particular as defined below, optionally substituted alkoxy, in particular as defined below, optionally substituted alkoxycarbonyl, in particular as defined below, optionally substituted acyl, in particular as defined below, halogen, in particular as defined below, optionally substituted amino, in particular as defined below, optionally substituted aminocarbonyl, in particular as defined below, and cyano.

Halogen includes here and within to the context of the present invention, fluorine, chlorine, bromine and iodine, preferably fluorine or chlorine.

In the above defined alkyl groups, optionally one or more, more preferably 1 to 3 carbon atoms can furthermore be replaced with hetero-analogous groups that contain nitrogen, oxygen or sulphur. This means, in particular, that, for example, one or more, preferably 1 to 3, still more preferred one (1) methylene group (—$CH_2$—) can be replaced in the alkyl groups by —NH—, —$NR_4$—, —O— or —S—, wherein $R_4$ is optionally substituted alkyl as defined above, preferably $C_1$-$C_6$ alkyl, such as methyl or ethyl, optionally substituted with 1 to 3 substituents, such as fluorine, chlorine, hydroxy or alkoxy.

Examples of alkyl residues having 1 to 8 carbon atoms include: a methyl group, an ethyl group, an n-propyl group, an i-propyl group, an n-butyl group, an i-butyl group, a sec-butyl group, a t-butyl group, an n-pentyl group, an i-pentyl group, a sec-pentyl group, a t-pentyl group, a 2-methylbutyl group, an n-hexyl group, a 1-methylpentyl group, a 2-methylpentyl group, a 3-methylpentyl group, a 4-methylpentyl group, a 1-ethylbutyl group, a 2-ethylbutyl group, a 3-ethylbutyl group, a 1,1-dimethylbutyl group, a 2,2-dimethylbutyl group, a 3,3-dimethylbutyl group, a 1-ethyl-1-methylpropyl group, an n-heptyl group, a 1-methylhexyl group, a 2-methylhexyl group, a 3-methylhexyl group, a 4-methylhexyl group, a 5-methylhexyl group, a 1-ethylpentyl group, a 2-ethylpentyl group, a 3-ethylpentyl group, a 4-ethylpentyl group, a 1,1-dimethylpentyl group, a 2,2-dimethylpentyl group, a 3,3-dimethylpentyl group, a 4,4-dimethylpentyl group, a 1-propylbutyl group, an n-octyl group, a 1-methylheptyl group, a 2-methylheptyl group, a 3-methylheptyl group, a 4-methylheptyl group, a 5-methylheptyl group, a 6-methylheptyl group, a 1-ethylhexyl group, a 2-ethylhexyl group, a 3-ethylhexyl group, a 4-ethylhexyl group, a 5-ethylhexyl group, a 1,1-dimethylhexyl group, a 2,2-dimethylhexyl group, a 3,3-dimethylhexyl group, a 4,4-dimethylhexyl group, a 5,5-dimethylhexyl group, a 1-propylpentyl group, a 2-propylpentyl group, etc. Those with 1 to 6 carbon atoms are preferred. Methyl, ethyl, n-propyl, isopropyl, sec-butyl and n-butyl are most preferred.

Examples of alkyl groups produced by replacement with one or more hetero-analogous groups, such as —O—, —S—, —NH— or —N($R_4$)— are preferably such groups in which one or more methylene groups (—$CH_2$—) are replaced with —O— while forming an ether group, such as methoxymethyl, ethoxymethyl, 2-methoxyethyl etc. Therefore, the definition of alkyl also includes, for example, alkoxyalkyl groups as defined below, which are produced from the above-mentioned alkyl groups by replacement of a methylene group with —O—. If, according to the invention, alkoxy group are additionally permitted as substituents of alkyl, several ether groups can also be formed in this manner (such as a —$CH_2$—O—$CH_2$—$OCH_3$— group). Thus, according to the invention, polyether groups are also comprised by the definition of alkyl.

Cycloalkyl groups with 3 to 8 carbon atoms preferably include: a cyclopropyl group, a cyclobutyl group, a cyclopentyl group, a cyclohexyl group, a cycloheptyl group, a cyclooctyl group, etc. A cyclopropyl group, a cyclobutyl group, a Cyclopentyl group and a Cyclohexyl group are preferred. The Cycloalkyl groups may optionally be substituted preferably with 1 to 2 substituents such as hydroxyl or $C_1$-$C_6$ alkoxycarbonyl.

The definition of the optionally substituted alkyl also includes alkyl groups which are substituted by the above mentioned cycloalkyl groups, such as cyclopropylmethyl, cyclobutylmethyl, cyclopentylmethyl or cyclohexylmethyl.

Heterocyclic alkyl groups according to the invention are preferably those formed by the replacement of methylene with hetero-analogous groups from cycloalkyl, and include, for example, saturated 5 or 6-membered heterocyclic residues, which may be attached via a carbon atom or a nitrogen atom, and which preferably may have 1 to 3, preferably 2 heteroatoms, especially O, N, such as tetrahydrofuryl, azetidine-1-yl, substituted azetidinyl, such as 3-hydroxyazetidin-1-yl, pyrrolidinyl, such as pyrrolidin-1-yl, substituted pyrrolidinyl, such as 3-hydroxypyrrolidin-1-yl, 2-hydroxypyrrolidin-1-yl 2-methoxycarbonylpyrrolidin-1-yl, 2-ethoxycarbonylpyrrolidin-1-yl, 2-methoxypyrrolidin-1-yl, 2-ethoxypyrrolidin-1-yl, 3-methoxycarbonylpyrrolidin-1-yl, 3-ethoxycarbonylpyrrolidin-1-yl, 3-methoxypyrrolidin-1-yl, 3-ethoxypyrrolidine-1-yl, piperidinyl, such as piperidin-1-yl, piperidin-4-yl, substituted piperidinyl, such as 4-methyl-1-piperidyl, 4-hydroxy-1-piperidyl, 4-methoxy-1-piperidyl, 4-ethoxy-1-piperidyl, 4-methoxycarbonyl-1-piperidyl, 4-ethoxycarbonyl-1-piperidyl, 4-carboxy-1-piperidyl, 4-acetyl-1-piperidyl, 4-formyl-1-piperidyl, 1-methyl-4-piperidyl, 4-hydroxy-2,2,6,6-tetramethyl-1-piperidyl, 4-(dimethylamino)-1-piperidyl, 4-(diethylamino)-1-piperidyl, 4-amino-1-piperidyl, 2-(hydroxymethyl)-1-piperidyl, 3-(hydroxymethyl)-1-piperidyl, 4-(hydroxymethyl)-1-piperidyl, 2-hydroxy-1-piperidyl, 3-hydroxy-1-piperidyl, 4-hydroxy-1-piperidyl, morpholin-4-yl, substituted morpholinyl, such as 2,6-dimethyl morpholin-4-yl, piperazinyl, such as piperazin-1-yl, substituted piperazinyl, such as 4-methylpiperazin-1-yl, 4-ethylpiperazin-1-yl, 4-ethoxycarbonylpiperazin-1-yl, 4-methoxycarbonylpiperazin-1-yl, or tetrahydropyranyl, such as tetrahydropyran-4-yl, and which can optionally be condensated with aromatic rings, and which may optionally be substituted, such as with 1 to 2 substituents such as hydroxy, halogen, C1-C6-alkyl, etc. The definition of the optionally substituted alkyl groups thus includes also alkyl groups, which are substituted by the above-defined heterocyclic groups, such as 3-(1-piperidyl)propyl, 3-pyrrolidin-1-ylpropyl, 3-morpholinopropyl, 2-morpholinoethyl, 2-tetrahydropyran-4-ylethyl, 3-tetrahydropyran-4-ylpropyl, 3-(azetidin-1-yl) propyl etc.

Examples of a linear or branched alkyl group substituted with halogen and having 1 to 8, preferably 1 to 6 carbon atoms include, in particular: a fluoromethyl group, a difluoromethyl group, a trifluoromethyl group, a chloromethyl group, a dichloromethyl group, a trichloromethyl group, a bromomethyl group, a dibromomethyl group, a tribromomethyl group, a 1-fluoroethyl group, a 1-chloroethyl group, a 1-bromoethyl group, a 2-fluoroethyl group, a 2-chloroethyl group, a 2-bromoethyl group, a 1,2-difluoroethyl group, a 1,2-dichloroethyl group, a 1,2-dibromoethyl group, a 2,2,2-trifluoroethyl group, a heptafluoroethyl group, a 1-fluoropropyl group, a 1-chloropropyl group, a 1-bromopropyl group, a 2-fluoropropyl group, a 2-chloropropyl group, a 2-bromopropyl group, a 3-fluoropropyl group, a 3-chloropropyl group, a 3-bromopropyl group, a 1,2-difluoropropyl group, a 1,2-dichloropropyl group, a 1,2-dibromopropyl group, a 2,3-difluoropropyl group, a 2,3-dichloropropyl group, a 2,3-dibromopropyl group, a 3,3,3-trifluoropropyl group, a 2,2,3,3,3-pentafluoropropyl group, a 2-fluorobutyl group, a 2-chlorobutyl group, a 2-bromobutyl group, a 4-fluorobutyl group, a 4-chlorobutyl group, a 4-bromobutyl group, a 4,4,4-trifluorobutyl group, a 2,2,3,3,4,4,4-heptafluorobutyl group, a perfluorobutyl group, a 2-fluoropentyl group, a 2-chloropentyl group, a 2-bromopentyl group, a 5-fluoropentyl group, a 5-chloropentyl group, a 5-bromopentyl group, a perfluoropentyl group, a 2-fluorohexyl group, a 2-chlorohexyl group, a 2-bromohexyl group, a 6-fluorohexyl group, a 6-chlorohexyl group, a 6-bromohexyl group, a perfluorohexyl group, a 2-fluoroheptyl group, a 2-chloroheptyl group, a 2-bromoheptyl group, a 7-fluoroheptyl group, a 7-chloroheptyl group, a 7-bromoheptyl group, a perfluoroheptyl group, etc.

Examples of an alkyl group substituted with hydroxy include the above-mentioned alkyl residues, which have 1 to 3 hydroxy residues, such as, for example hydroxymethyl, 2-hydroxyethyl, 3-hydroxypropyl, 4-hydroxybutyl, 5-hydroxypentyl, 6-hydroxyhexyl.

Optionally substituted aryl preferably includes according to the invention aromatic hydrocarbon residues with 6 to 14 carbon atoms (with no hetero atom in the aromatic ring system), for example: phenyl, naphthyl, phenanthrenyl and anthracenyl. The aforementioned aromatic groups may be unsubstituted or substituted. In case of substitution, they preferably have one or more, preferably one (1) or two (2) substituents, in particular halogen, hydroxy, alkyl, alkoxy, in each case as explained above or below. A preferred aromatic group is phenyl. A preferred alkyl substituted with an aromatic group (arylalkyl) is benzyl.

Optionally substituted aryl according to the present invention further includes optionally substituted heteroaryl, that is, heteroaromatic groups, such as for example: pyridyl, pyridyl-N-oxide, pyrimidyl, pyridazinyl, pyrazinyl, thienyl, furyl, pyrrolyl, pyrazolyl, imidazolyl, thiazolyl, oxazolyl or isoxazolyl, indolizinyl, indolyl, benzo[b]thienyl, benzo[b]furyl, indazolyl, quinolyl, isoquinolyl, naphthyridinyl, quinazolinyl. 5- or 6-membered aromatic heterocycles such as, for example pyridyl, pyridyl-N-oxide, pyrimidyl, pyridazinyl, furyl and thienyl are preferred. The aforementioned heteroaromatic groups may be unsubstituted or substituted. In case of substitution, they preferably have one or more, preferably one (1) or two (2) substituents, in particular halogen, hydroxy, alkyl, alkoxy, in each case as explained above or below. Preferred examples of an alkyl substituted with a heteroaromatic group (hetarylalkyl) are methyl, ethyl, or propyl, in each case substituted with a heteroaromatic group, such as thienylmethyl, pyridylmethyl etc.

Optionally substituted alkoxy (RO—) is formally derived from the above mentioned optionally substituted alkyl residues by adding an oxygen atom and includes in context with the present invention, for example, linear or branched alkoxy groups with up to 6 carbon atoms, such as a methoxy group, an ethoxy group, an n-propyloxy group, an i-propyloxy group, an n-butyloxy group, an i-butyloxy group, a sec-butyloxy group, a t-butyloxy group, an n-pentyloxy group, an i-pentyloxy group, a sec-pentyloxy group, a t-pentyloxy group, a 2-methylbutoxy group, an n-hexyloxy group, an i-hexyloxy group, a t-hexyloxy group, a sec-hexyloxy group, a 2-methylpentyloxy group, a 3-methylpentyloxy group, a 1-ethylbutyloxy group, a 2-ethylbutyloxy group, a 1,1-dimethylbutyloxy group, a 2,2-dimethylbutyloxy group, a 3,3-dimethylbutyloxy group, a 1-ethyl-1-methylpropyloxy group, etc. A methoxy group, an ethoxy group, an n-propyloxy group, an i-propyloxy group, an n-butyloxy group, an i-butyloxy group, a sec-butyloxy group, a t-butyloxy group, etc., are preferred. The alkoxy groups may optionally be substituted, such as with the above possible substituents for alkyl.

Methoxy, ethoxy, n-propoxy, n-butoxy, etc. are preferred alkoxy.

Optionally substituted alkoxycarbonyl (RO—CO—) groups are formally derived from the above alkyl groups by adding a —OC(O)— residue under formation of an optionally substituted alkyloxycarbonyl residue. In that regard reference can be made to the definition of the above-described alkyl groups. As an alternative optionally substituted alkoxycarbonyl (RO—CO—) groups are derived from the aforementioned alkoxy groups by the addition of a carbonyl group. Methoxycarbonyl, ethoxycarbonyl, n-propoxycarbonyl, n-butoxycarbonyl tert.-butoxycarbonyl etc. are preferred alkoxycarbonyl, which may all be substituted as the above defined alkyl groups.

Optionally substituted amino according to the invention includes preferably: amino (—NH$_2$), optionally substituted mono- or dialkylamino (RHN—, (R)$_2$N), wherein with respect to the definition of optionally substituted alkyl it can be referenced to the above definition. Further included are optionally substituted mono- or diarylamino radicals or mixed optionally substituted alkyl aryl amino radicals, wherein with respect to the definition of optionally substituted alkyl or aryl reference can be made to the above definition. Such groups include, for example, methylamino, dimethylamino, ethylamino, hydroxyethylamino, such as 2-hydroxyethylamino, diethylamino, phenylamino, methylphenylamino etc. Particularly preferred is ethylamino. Optionally substituted amino further includes an optionally substituted cyclic amino, such as optionally substituted 5 or 6-membered cyclic amino that may contain further hetero atoms such as N, O, S, preferably O. Examples of such cyclic amino groups include: the above-mentioned nitrogen-containing heterocyclic groups which are attached via a nitrogen atom, such as piperidin-1-yl, 4-hydroxy-piperidin-1-yl, 2-(methoxycarbonyl)pyrrolidin-1-yl, pyrrolidin-1-yl, morpholin-4-yl, etc.

Optionally substituted amino carbonyl according to the invention can be formally derived from optionally substituted amino, as explained before, by adding a carbonyl residue ((R)$_2$N—C(=O)—). Therein optionally substituted amino preferably includes according to the invention: amino (—NH$_2$), optionally substituted mono- or dialkylamino (RHN—, (R)$_2$N—) for which with regard to the definition of optionally substituted alkyl reference can be made to the above definition. Furthermore included are optionally substituted mono- or diarylamino groups or mixed optionally substituted alkylarylamino groups, for which as regards the definition of optionally substituted alkyl or aryl reference can be made to the above definitions. Such groups include, for example methylamino, Dimethylamino, ethylamino, hydroxyethylamino, such as 2-hydroxyethlyamino, Diethylamino, phenylamino, methylphenylamino etc.

Optionally substituted amino further includes an optionally substituted cyclic amino, such as optionally substituted 5 or 6-membered cyclic amino that may contain further hetero atoms such as N, O, S, preferably O. Examples of such cyclic amino groups include the above-mentioned nitrogen-containing heterocyclic groups bonded through a nitrogen atom, such as piperidin-1-yl, 4-hydroxy-piperidin-1-yl, 2-(methoxycarbonyl)pyrrolidin-1-yl, pyrrolidin-1-yl, Morpholin-4-yl etc.

Examples of optionally substituted aminocarbonyl include therefore: Carbamoyl ($H_2NC(=O)-$), optionally substituted mono- or dialkylaminocarbonyl ($RHNC(=O)$, $(R)_2NC(=O)-$), wherein reference can be made to the above definition of optionally substituted alkyl. Furthermore are included optionally substituted mono- or diarylaminocarbonyl residues or mixed, optionally substituted alkylarylaminocarbonyl residues, wherein reference can be made to the above definitions of optionally substituted alkyl and aryl. Preferred substituted aminocarbonyl groups comprise up to 14 carbon atoms. Such groups include for example methylaminocarbonyl, dimethylaminocarbonyl, ethylaminocarbonyl, diethylaminocarbonyl, phenylaminocarbonyl, diphenylaminocarbonyl, methylphenylamino-carbonyl etc.

In a preferred embodiment, $R_1$ and $R_2$ or $R_2$ and $R_3$ form together with the carbon atoms to which they are attached a 5- or 6-membered carbocyclic ring.

Examples of the aforementioned ring formation of the substituents $R_1$ and $R_2$ or $R_2$ and $R_3$ as represented schematically by the following formulas:

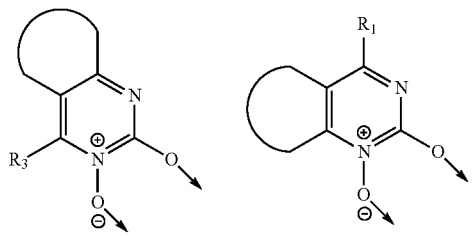

include in particular:
compounds in which $R_1$ and $R_2$ or $R_2$ and $R_3$ together preferably represent a propylene ($-CH_2-CH_2-CH_2-$) or a butylene ($-CH_2-CH_2-CH_2-CH_2-$) group, in which optionally one methylene group ($-CH_2-$) respectively can be replaced with $-O-$, $-NH-$ or $-NR_4-$, wherein $R_4$ is defined as mentioned above and wherein the groups formed by $R_1$ and $R_2$ or $R_2$ or $R_3$ optionally can furthermore respectively be substituted by one to three substituents selected from the group consisting of hydroxy, oxo, $C_1$-$C_4$ alkoxy, amino and mono- or di-($C_1$-$C_4$-alkyl)amino.

Exemplary ligands are the following:

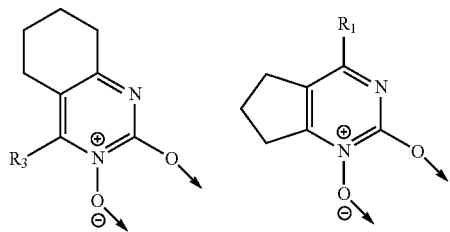

wherein $R_1$ and $R_3$ are each as described above.

In another particularly preferred embodiment of iron (III) complex compounds according to the invention $R_1$, $R_2$, $R_3$ are identical or different and are selected from the group consisting of hydrogen and alkyl, with the proviso that at least one, preferably two of the substituents $R_1$, $R_2$, and $R_3$ are alkyl. Alkyl is preferably as mentioned above, especially straight-chained or branched, preferably, unsubstituted alkyl having up to 6, preferably up to 4 carbon atoms. Still more preferred are iron (III) complex compounds wherein $R_2$ is hydrogen, and $R_1$ and $R_3$ are each the same or different and are selected from alkyl as mentioned above.

The iron(III) complex compounds of the formula (II) are particularly preferred:

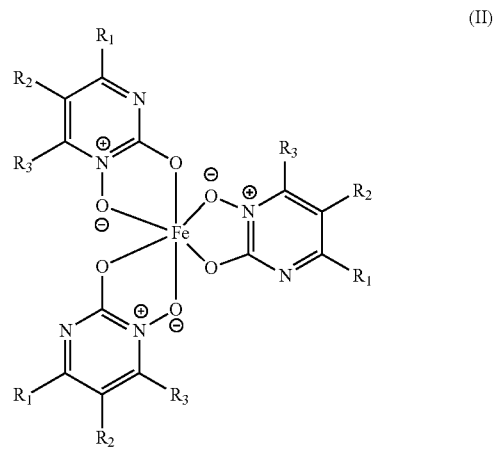

wherein $R_1$, $R_2$ and $R_3$ are each defined as above or preferably as defined below.

Furthermore, preferably $R_1$, $R_2$ and $R_3$ are the same or different and are selected from:
hydrogen,
C1-6-alkyl, preferably as presented above,
halogen, preferably as presented above,
C3-6-cycloalkyl, preferably as presented above,
C3-6-cycloalkyl-C1-4-alkyl, preferably as presented above,
C1-4-alkoxy-C1-4-alkyl, preferably as presented above,
C1-4-alkoxycarbonyl, preferably as presented above,
C1-4-mono- or dialkylaminocarbonyl, preferably as presented above,
aminocarbonyl or carbamoyl ($H_2NCO-$) respectively,
hydroxy-C1-4-alkyl, preferably as presented above, and
halogen-C1-4-alkyl, preferably as presented above.

Particularly preferably $R_1$, $R_2$ and $R_3$ are the same or different and are selected from: hydrogen, halogen and C1-6-alkyl, preferably as presented above, in particular hydrogen, chlorine, methyl, ethyl and propyl, in particular i-propyl, butyl, especially sec-butyl. Most preferably, $R_1$, $R_2$ and $R_3$ are selected from: hydrogen, methyl and ethyl.

In a further embodiment of the invention there are provided the iron (III)-pyrimidin-2-ol 1-oxide-complex compounds in solid form. The term "solid form" means here in particular in contrast to the dissolved form, in which the iron (III)-pyrimidin-2-ol 1-oxide-complex compounds are present dissolved in a solvent such as water. The term "solid form" means also that the iron (III)-pyrimidin-2-ol 1-oxide-complex compounds at room temperature (23° C.) are present in solid form. The iron (III)-pyrimidin-2-ol 1-oxide-complex compounds can be present in an amorphous, crystalline or partially crystalline form. Also, the iron (III)-pyrimidin-2-ol 1-oxide-complex compounds of the invention may exist as hydrates, in particular as crystalline hydrates, such as the monohydrate, in particular as a crystalline monohydrate.

It is clear to the person skilled in the art that the ligands according to the invention

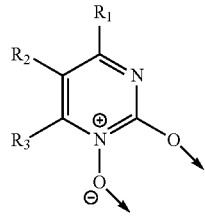

arise from the corresponding pyrimidine-2-ol-1-oxide compounds:

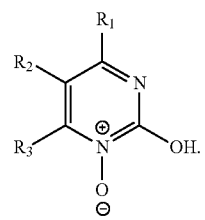

In the pyrimidine-2-ol-1-oxide compounds there is a keto-enol-tautomerism, wherein the equilibrium state is determined by various factors.

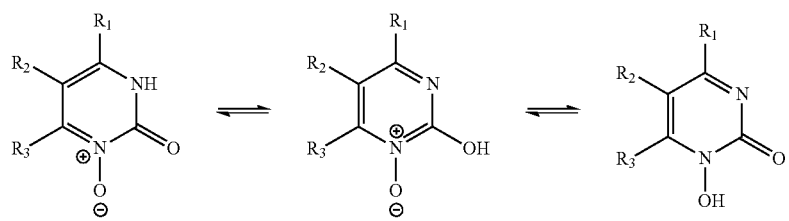

The ligand is formally obtained by cleavage of a proton from the corresponding pyrimidine-1-oxide compounds:

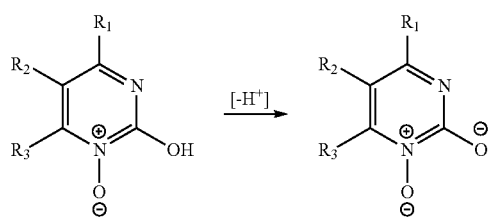

so formally carries a single negative charge.

Furthermore it is clear to a person skilled in the art that the pyrimidine-2-ol-1-oxide compounds as used according to the present invention can be drawn by different notations (a, b and c), but all include the same issue of the N-oxide.

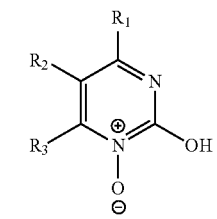

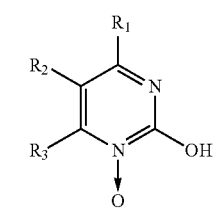

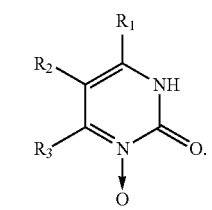

The same applies for the corresponding deprotonated form of the pyrimidine-2-ol-1-oxide ligand compounds. Within the scope of the present invention all tautomeric forms are included, even if only one of the mesomeric formulas is drawn.

Depending on the substituent $R_1$, $R_2$, $R_3$ they can also participate in the tautomeric resonance structures in the pyrimidine-2-ol-1-oxide ligand. By way of example, the 4-amino compounds can be mentioned. For example:

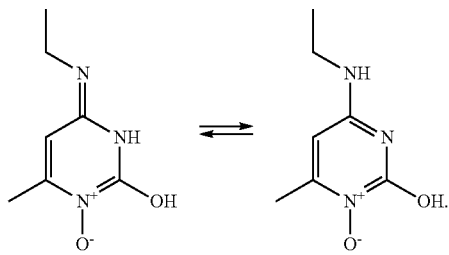

All such tautomers are included within the scope of the invention.

Optionally substituted amino preferably is in the position of $R_1$, ie, in the 4-position of the pyrimidine ligand.

The iron(III) pyrimidine-2-ol-oxide complex compounds, in particular such as of the general formula (II) or the corresponding pyrimidine-2-ol-1-oxide ligands, respectively, can be present in the form of various isomers or tautomers. Isomeric forms include, for example, regioisomers which differ in the position of the ligands relative to one another, including so-called optical isomers that have an image/mirror image relationship to one another. If asymmetric carbon atoms are present, the ligands can be present in the form of optical isomers which have an image/mirror image relationship to one another, and include pure enantiomers, mixtures of the enantiomers, in particular racemates. Enantiomerically pure ligands can be obtained, as is known to the person skilled in the art, by optical resolution methods, such as reaction with chiral reagents to form diastereomers, separation of the diastereomers and release of the enantiomers. Examples of tautomeric resonance structures, which are also included according to the invention have been shown above as an example.

Furthermore, in particular the following are preferred embodiments of the invention:
(In the present invention, the digits 1-6 in "1-6C" or "1-4" in "1-4C" or "C1-4" etc. in each case signify the number of the carbon atoms of the subsequent hydrocarbon group designations).

$R_1$, $R_2$ and $R_3$ are selected from the group consisting of:
hydrogen,
halogen,
mono- or di(1-6C-alkyl)amino,
1-6C-alkyl, (i.e. alkyl with 1 to 6 carbon atoms),
3-6C-cycloalkyl,
3-6C-cycloalkyl-1-4C-alkyl,
1-4C-alkoxy-1-4C-alkyl,
hydroxy-1-4C-alkyl,
fluoro-1-4C-alkyl;
or $R_1$ and $R_2$ together form a propylene (—$CH_2$—$CH_2$—$CH_2$), butylene (—$CH_2$—$CH_2$—$CH_2$—$CH_2$—), azabutylene or oxabutylene group;
or $R_2$ and $R_3$ together form a propylene (—$CH_2$—$CH_2$—$CH_2$—)—, butylene (—$CH_2$—$CH_2$—$CH_2$—$CH_2$—), azabutylene or oxabutylene group
or $R_1$ and $R_2$ together with a carbon atom to which they are bonded, form an unsaturated ring, which may optionally contain one or more further hetero atoms,
or $R_2$ and $R_3$ together with a carbon atom to which they are bonded, form an unsaturated ring, which may optionally contain one or more further hetero atoms,
or pharmaceutically acceptable salts thereof.

Preferably, the aforementioned substituent groups are defined as follows:
1-6C-alkyl preferably includes straight-chained or branched alkyl groups with 1 to 6 carbon atoms. Examples therefore can be methyl, ethyl, n-propyl, iso-propyl, n-butyl, iso-butyl, sec-butyl, tert-butyl n-pentyl, iso-pentyl, neo-pentyl, n-hexyl, iso-hexyl and neo-hexyl.
3-6C-Cycloalkyl preferably includes cycloalkyl 1 to 6 carbon atoms, such as cyclopropyl, cyclobutyl, cyclopentyl, cyclohexyl.
3-6C-cycloalkyl-1-4C-alkyl preferably includes a 1-6C-alkyl group described above, substituted with a 3-6C-cycloalkyl group described above. Examples therefor can be a cyclopropylmethyl, cyclopentylmethyl and cyclohexylmethyl group.
1-3C-alkoxy-carbonyl-1-6C-alkyl, preferably includes a 1-6C-alkyl group described above, which is linked to a carbonyl group which is present with a 1-3C alkoxy group as a carboxylic acid ester. Examples therefor can be methoxycarbonylmethyl, ethoxycarbonylmethyl, methoxycarbonylethyl, ethoxycarbonylethyl and isopropoxycarbonylmethyl.

1-4C-alkoxy preferably includes a 1-4C-alkoxy group, in which an oxygen atom is connected to a straight or branched alkyl chain with 1-4 carbon atoms. Examples of this group can be methoxy, ethoxy, propoxy and isobutoxy.

1-4C-alkoxy-1-4C-alkyl preferably includes a 1-4C-alkoxy group described above, which is substituted with a 1-4C-alkyl group described above. Examples of this group can be methoxyethyl, ethoxypropyl, methoxypropyl, isobutoxymethyl.

Hydroxy-1-4C-alkyl includes a 1-4C-alkyl group described above, which is substituted with a hydroxy group. Examples therefor can be hydroxyethyl, hydroxybutyl and hydroxyisopropyl.

Fluoro-1-4C-alkyl includes a 1-4C-alkyl group described above, which is substituted with one to three fluorine atoms. Examples therefor can by trifluoromethyl and trifluoroethyl.

Halogen signifies F, Cl, Br, I.

Particularly preferred are:
$R_1$, $R_2$ and $R_3$ are selected from the group consisting of:
hydrogen,
halogen,
1-6C-alkyl,
1-4C-alkoxy-1-4C-alkyl,
hydroxy-1-4C-alkyl;
or $R_1$ and $R_2$ together form a propylene (—$CH_2$—$CH_2$—$CH_2$), butylen (—$CH_2$—$CH_2$—$CH_2$—$CH_2$—), azabutylene or oxabutylene group;
or $R_2$ and $R_3$ together form a propylene (—$CH_2$—$CH_2$—$CH_2$), butylene (—$CH_2$—$CH_2$—$CH_2$—$CH_2$—), azabutylene or oxabutylene group,
or $R_1$ and $R_2$ together with a carbon atom on which they are bonded, form an unsaturated ring which may optionally contain further hetero atoms,
or $R_2$ and $R_3$ together with a carbon atom to which they are bonded, form an unsaturated ring which may optionally comprise further hetero atoms.

Particularly preferably:
$R_1$, $R_2$ and $R_3$ are selected from the group consisting of:
hydrogen,
1-6C-alkyl;
1-4C-alkoxy-1-4C-alkyl
or $R_1$ and $R_2$ together form a propylene (—$CH_2$—$CH_2$—$CH_2$) or butylene (—$CH_2$—$CH_2$—$CH_2$—$CH_2$—) group;
or $R_2$ and $R_3$ together form a propylene (—$CH_2$—$CH_2$—$CH_2$) or butylene (—$CH_2$—$CH_2$—$CH_2$—$CH_2$—) group
or $R_1$ and $R_2$ together with a carbon atom to which they are bonded form an unsaturated ring which may comprise one further nitrogen atom,
or $R_2$ and $R_3$ together with a carbon atom to which they are bonded form an unsaturated ring which may comprise a further nitrogen atom.

Particularly preferred complex compounds of the general formula (II) are described in the examples.

The invention further relates to a method for the preparation of the iron(III) complex compounds according to the invention which comprises the reaction of a pyrimidine-2-ol-1-oxide of formula (III) with an iron(III) salt.

Pyrimidin-2-ol-1-oxides as the starting compounds include in particular those of the formula (III):

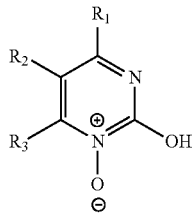

wherein $R_1$, $R_2$ and $R_3$ are defined as above, to the tautomeric resonance structures of which it has been referred to.

Examples of suitable iron(III) salts include: iron(III) chloride, iron(III) acetate, iron(III) sulfate, iron(III) nitrate and iron(III) acetylacetonate, among which iron(III) chloride is preferred.

A preferred method is shown in the following scheme:

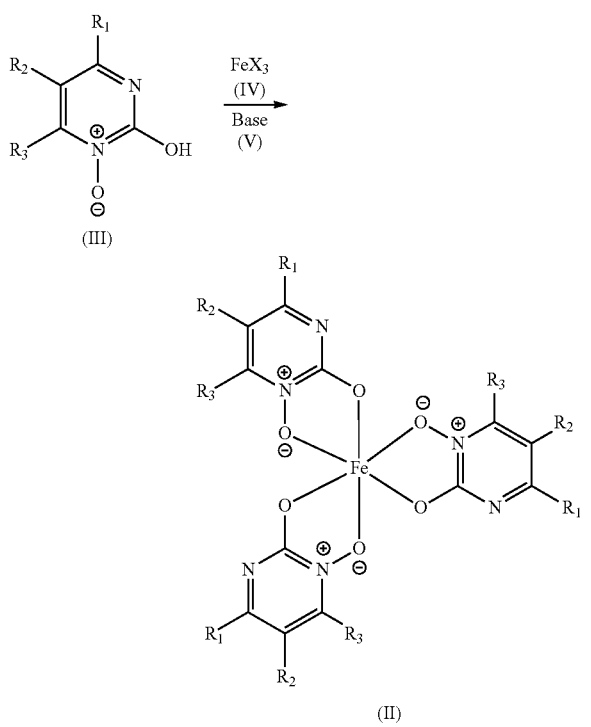

wherein $R_1$, $R_2$ and $R_3$ are as defined above, X is an anion such as halogenide, such as chloride, a carboxylate, such as acetate, sulphate, nitrate and acetylacetonate and base is a common organic or inorganic base.

In the method according to the invention, preferably 3 eq pyrimidine-2-ol-1-oxide (III), using suitable iron(III) salts (IV) (in this case Fe(III) chloride, Fe(III) acetate, Fe(III) sulphate and Fe(III) acetylacetonate are particularly suitable), are reacted under standard conditions to form the corresponding complexes of the general formula (II). In this case, the synthesis is carried out under the pH conditions optimal for complex formation. The optimum pH value is set by adding a base (V); in this case, the use of sodium hydroxide, sodium carbonate, sodium hydrogen carbonate, sodium methanolate, potassium hydroxide, potassium carbonate, potassium hydrogen carbonate or potassium methanolate is particularly suitable.

The ligands (III) required for the preparation of the complexes where prepared according to the following synthesis method (analogue tetrahedron 1967, 23, 353-357). For this purpose, the commercially available or synthesised 1,3-dicarbonyl compounds of the general formula (IV) were reacted under standard conditions with hydroxy urea (V) to form ligands of the general formula (III). When using unsymmetrical 1-3-dicarbonyl compounds in this synthesis, this results almost always in the occurrence of the corresponding regioisomers (IIIa), which can be separated by standard methods which are well known to a person skilled in the art. For certain substitution patterns for $R_1$, $R_2$ and $R_3$ (IIIa) can also represent the main product and, in these cases, then is the synthesis access to the respective substitution patterns.

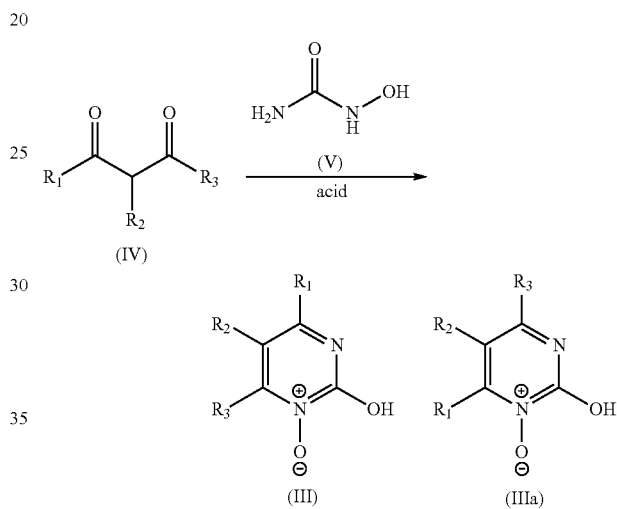

Analogously, it is also possible to use slightly modified synthesis routes for the preparation of the respective ligands of the general formula (III). I.e., in the synthesis of Ohkanda et al. (Bull. Chem. Soc. Jpn, 1993, 66, 841-847) the benzyl protected urea according to formula (V-Bn) is cyclized under standard conditions with the respective 1,3-dicarbonyl compounds (IV) to form the corresponding benzyl protected product (III-Bn), wherein the subsequent cleavage leads to the desired product (III). In this alternative synthesis route it comes to the occurrence of (IIIa), too.

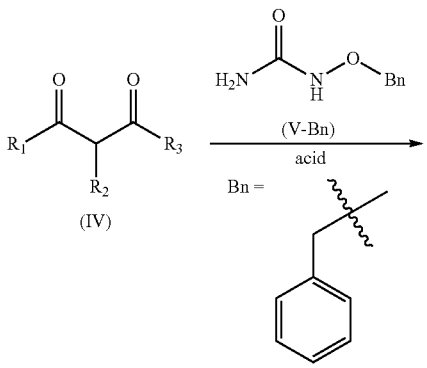

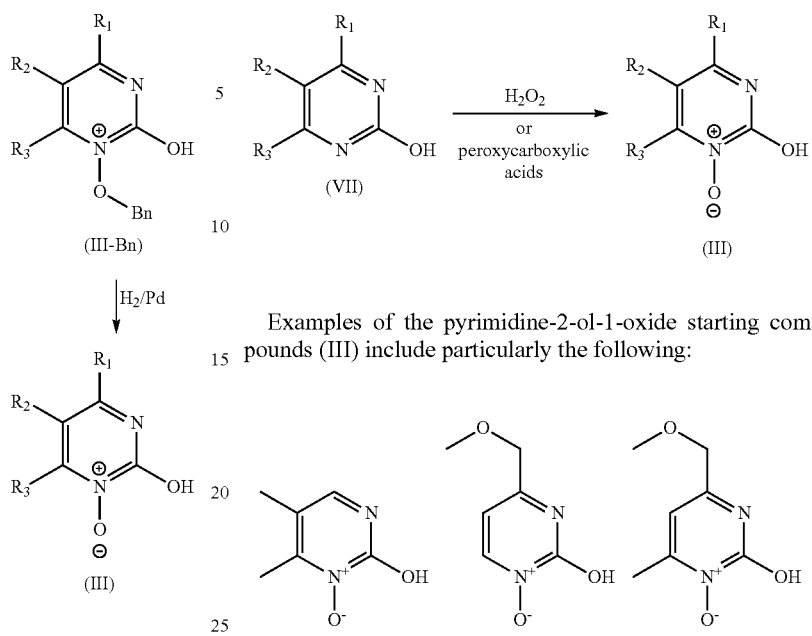

For ligands in which one or both of the radicals $R_1$ and $R_3$ are hydrogen, a slightly modified synthesis was carried out. Herein the corresponding protected 1,3-dicarbonyl compounds such as for example those of the general formula (VI) have been reacted similarly with hydroxyurea (V) under acidic standard conditions. In this case R is preferably methyl or ethyl.

Herein too, the product ratio of the two forming pyrimidine-2-ol-1-oxides (IIIc) and (IIId) is controlled by the choice of the radicals $R_1$ and $R_2$. The separation is then performed under standard conditions familiar to those skilled in the art.

In general, the preparation of the pyrimidine-2-ol-oxide (III) can be as well carried out by other synthesis routes familiar to a skilled person. Thus, for example, there is the possibility to react the respective substituted pyrimidines (VII) with suitable oxidizing agents, such as hydrogen peroxide or peroxycarboxylic acids, to form the desired products of general formula (III) (e.g. analogous to Can. J. Chem. 1984, 62, 1176-1180).

Examples of the pyrimidine-2-ol-1-oxide starting compounds (III) include particularly the following:

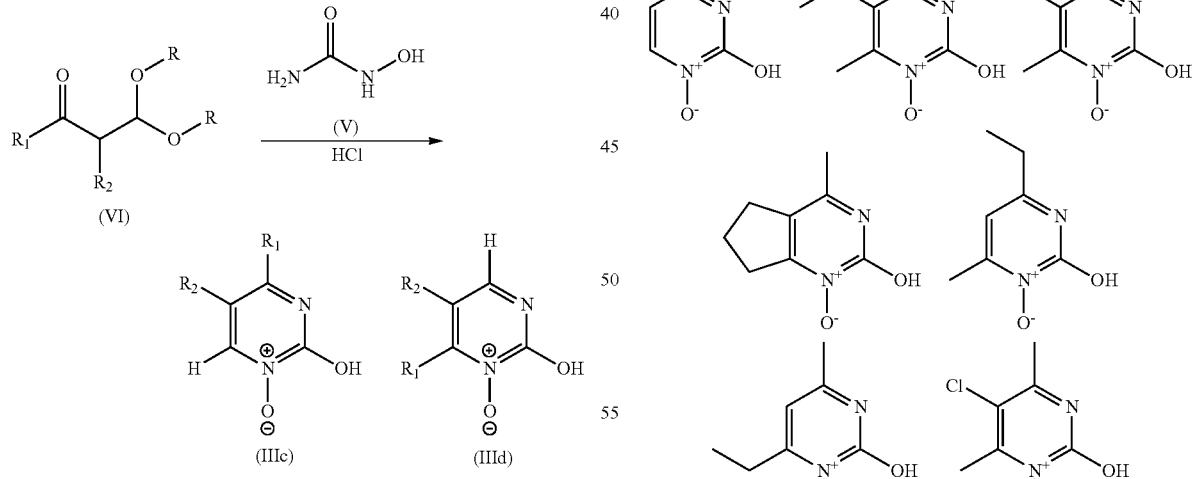

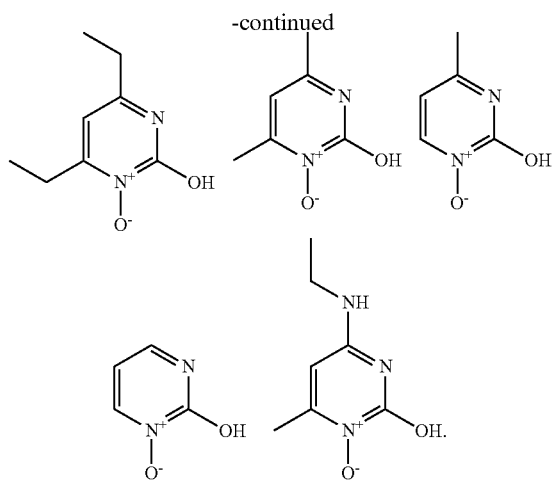

From these compounds the ligands of the iron complex compounds according to the present invention are derived by simple deprotonation at the hydroxy group.

Pharmaceutically acceptable salts of the compounds according to the invention in which the iron(III) complex formally carries a positive charge include, for example, salts with suitable anions, such as carboxylates, sulfonates, sulfates, chlorides, bromides, iodides, phosphates, tartates, methanesulfonates, hydroxethanesulfonates, glycinates, maleates, propionates, fumarates, tulouenesulfonates, benzene sulfonates, trifluoroacetates, naphthalenedisulfonates-1,5, salicylates, benzoates, lactates, salts of malic acid, salts of 3-hydroxy-2-naphthoic acid-2, citrates and acetates.

Pharmaceutically acceptable salts of the compounds according to the invention in which the iron(III) complex formally carries a negative charge include, for example, salts with suitable pharmaceutically acceptable bases, such as, for example, salts with alkaline or alkaline-earth hydroxides, such as NaOH, KOH, Ca(OH)$_2$, Mg(OH)$_2$ etc., amine compounds such as ethylamine, diethylamine, triethylamine, ethyldiisopropylamine, ethanolamine, diethanolamine, triethanolamine, methylglucamine, dicyclohexylamine, dimethylaminoethanol, procaine, dibenzylamine, N-methylmorpholine, arginine, lysine, ethylenediamine, N-methylpiperidin, 2-amino-2-methyl-propanol-(1), 2-amino-2-methyl-propandiol-(1,3), 2-amino-2-hydroxyl-methyl-propandiol-(1,3) (TRIS) etc.

The water-solubility or the solubility in physiological saline solution and thus, optionally, also the efficacy of the compounds according to the invention can be significantly influenced by salt formation in general, specifically by the choice of the counterion.

Preferably, the compounds according to the invention constitute neutral complex compounds.

Advantageous Pharmacological Effects:

Surprisingly, the inventors found that the iron(III) pyrimidine-2-ol-1-oxide complex compounds which are the subject matter of the present invention and which are represented, in particular, by the general structural formula (II), are stable bioavailable iron complexes and suitable for use as a medicament for the treatment and prophylaxis of iron deficiency symptoms and iron deficiency anemias the symptoms accompanying them.

The medicaments containing the compounds according to the invention are suitable for use in human and veterinary medicine.

The compounds according to the invention are thus also suitable for preparing a medicament for the treatment of patients suffering from symptoms of an iron deficiency anemia, such as, for example: fatigue, listlessness, lack of concentration, low cognitive efficiency, difficulties in finding the right words, forgetfulness, unnatural pallor, irritability, acceleration of heart rate (tachycardia), sore or swollen tongue, enlarged spleen, desire for strange foods (pica), headaches, lack of appetite, increased susceptibility to infections or depressive moods.

The iron(III) complex compounds according to the invention are furthermore suitable for the treatment of iron deficiency anemia in pregnant women, latent iron deficiency anemia in children and adolescents, iron deficiency anemia caused by gastrointestinal abnormalities, iron deficiency anemia due to blood loss, such as gastrointestinal hemorrhage (e.g. due to ulcers, carcinoma, hemorrhoids, inflammatory disorders, taking of acetylsalicylic acid), iron deficiency anemia caused by menstruation, iron deficiency anemia caused by injuries, iron deficiency anemia due to sprue, iron deficiency anemia due to reduced dietary iron uptake, in particular in selectively eating children and adolescents, immunodeficiency caused by iron deficiency anemia, brain function impairment caused by iron deficiency anemias, restless leg syndrome caused by iron deficiency anemias, iron deficiency anemias in the case of cancer, iron deficiency anemias caused by chemotherapies, iron deficiency anemias triggered by inflammation (AI), iron deficiency anemias in the case of congestive cardiac insufficiency (CHF; congestive heart failure), iron deficiency anemias in the case of chronic renal insufficiency stage 3-5 (CDK 3-5; chronic kidney diseases stage 3-5), iron deficiency anemias triggered by chronic inflammation (ACD), iron deficiency anemias in the case of rheumatoid arthritis (RA), iron deficiency anemias in the case of systemic lupus erythematosus (SLE) and iron deficiency anemias in the case of inflammatory bowel diseases (IBD).

Administration can take place over a period of several months until the iron status is improved, which is reflected, for example, by the hemoglobin level, transferrin saturation and the serum ferritin level of the patients, or until the desired improvement of the state of health affected by iron deficiency anemia.

The preparation according to the invention can be taken by children, adolescents and adults.

The applied compounds according to the invention can in this case be administered both orally as well as parentally. Oral administration is preferred.

The compounds according to the invention and the aforementioned combinations of the compounds according to the invention with other active substances or medicines can thus be used, in particular, for the preparation of medicaments for the treatment of iron deficiency anemia, such as iron deficiency anemia in pregnant women, latent iron deficiency anemia in children and adolescents, iron deficiency anemia caused by gastrointestinal abnormalities, iron deficiency anemia due to blood loss, such as gastrointestinal hemorrhage (e.g. due to ulcers, carcinoma, hemorrhoids, inflammatory disorders, taking of acetylsalicylic acid), menstruation, injuries, iron deficiency anemia due to sprue, iron deficiency anemia due to reduced dietary iron uptake, in particular in selectively eating children and adolescents, immunodeficiency caused by iron deficiency anemia, brain function impairment caused by iron deficiency anemia, restless leg syndrome.

The application according to the invention leads to an improvement of the iron, hemoglobin, ferritin and transferrin levels, which, in particular in children and adolescents, but also in adults, is accompanied by an improvement in short-term memory tests (STM), long-term memory tests (LTM), Ravens' progressive matrices test, in the Wechsler adult intelligence scale (WAIS) and/or in the emotional coefficient (Baron EQ-i, YV test, youth version), or to an improvement of the neutrophile level, the antibody levels and/or lymphocyte function.

Furthermore, the present invention relates to pharmaceutical compositions comprising one or more of the compounds according to the invention, in particular according to the formula (II), as well as optionally one or more further pharmaceutically effective compounds, as well as optionally one or more pharmacologically acceptable carriers and/or auxiliary substances and/or solvents. The said pharmaceutical compositions contain, for example up to 99 weight-% or up to 90 weight-% or up to 80 weight-% of the compounds of the invention, the remainder being each formed by pharmacologically acceptable carriers and/or auxiliaries and/or solvents.

These are common pharmaceutical carriers, auxiliary substances or solvents. The above-mentioned pharmaceutical compositions are suitable, for example, for intravenous, intraperitoneal, intramuscular, intravaginal, intrabuccal, percutaneous, subcutaneous, mucocutaneous, oral, rectal, transdermal, topical, intradermal, intragasteral or intracutaneous application and are provided, for example, in the form of pills, tablets, enteric-coated tablets, film tablets, layer tablets, sustained release formulations for oral, subcutaneous or cutaneous administration (in particular as a plaster), depot formulations, dragees, suppositories, gels, salves, syrup, granulates, suppositories, emulsions, dispersions, microcapsules, microformulations, nanoformulations, liposomal formulations, capsules, enteric-coated capsules, powders, inhalation powders, microcrystalline formulations, inhalation sprays, epipastics, drops, nose drops, nose sprays, aerosols, ampoules, solutions, juices, suspensions, infusion solutions or injection solutions etc.

Preferably, the compounds according to the invention as well as pharmaceutical compositions containing such compounds are applied orally, although other forms, such as parentally, in particular intravenously, are also possible.

For this purpose, the compounds according to the invention are preferably provided in pharmaceutical compositions in the form of pills, tablets, enteric-coated tablets, film tablets, layer tablets, sustained release formulations for oral administration, depot formulations, dragees, granulates, emulsions, dispersions, microcapsules, microformulations, nanoformulations, liposomal formulations, capsules, enteric-coated capsules, powders, microcrystalline formulations, epipastics, drops, ampoules, solutions, suspensions, infusion solutions or injection solutions.

The compounds according to the invention can be administered in pharmaceutical compositions which may contain various organic or inorganic carrier and/or auxiliary materials as they are customarily used for pharmaceutical purposes, in particular for solid medicament formulations, such as, for example, excipients (such as saccharose, starch, mannitol, sorbitol, lactose, glucose, cellulose, talcum, calcium phosphate, calcium carbonate), binding agents (such as cellulose, methylcellulose, hydroxypropylcellulose, polypropyl pyrrolidone, gelatine, gum arabic, polyethylene glycol, saccharose, starch), disintegrating agents (such as starch, hydrolyzed starch, carboxymethylcellulose, calcium salt of carboxymethylcellulose, hydroxypropyl starch, sodium glycol starch, sodium bicarbonate, calcium phosphate, calcium citrate), lubricants (such as magnesium stearate, talcum, sodium laurylsulfate), a flavorant (such as citric acid, menthol, glycin, orange powder), preserving agents (such as sodium benzoate, sodium bisulfite, methylparaben, proylparaben), stabilizers (such as citric acid, sodium citrate, acetic acid and multicarboxylic acids from the titriplex series, such as, for example, diethylenetriaminepentaacetic acid (DTPA), suspending agents (such as methylcellulose, polyvinyl pyrrolidone, aluminum stearate), dispersing agents, diluting agents (such as water, organic solvents), beeswax, cocoa butter, polyethylene glycol, white petrolatum, etc.

Liquid medicament formulations, such as solvents, suspensions and gels usually contain a liquid carrier, such as water and/or pharmaceutically acceptable organic solvents. Furthermore, such liquid formulations can also contain pH-adjusting agents, emulsifiers or dispersing agents, buffering agents, preserving agents, wetting agents, gelatinizing agents (for example methylcellulose), dyes and/or flavouring agents. The compositions may be isotonic, that is, they can have the same osmotic pressure as blood. The isotonicity of the composition can be adjusted by using sodium chloride and other pharmaceutically acceptable agents, such as, for example, dextrose, maltose, boric acid, sodium tartrate, propylene glycol and other inorganic or organic soluble substances. The viscosity of the liquid compositions can be adjusted by means of a pharmaceutically acceptable thickening agent, such as methylcellulose. Other suitable thickening agents include, for example, xanthan gum, carboxymethylcellulose, hydroxypropylcellulose, carbomer and the like. The preferred concentration of the thickening agent will depend on the agent selected. Pharmaceutically acceptable preserving agents can be used in order to increase the storage life of the liquid composition. Benzyl alcohol can be suitable, even though a plurality of preserving agents including, for example, paraben, thimerosal, chlorobutanol and benzalkonium chloride can also be used.

The active substance can be administered, for example, with a unit dose of 0.001 mg/kg to 500 mg/kg body weight, for example 1 to 4 times a day. However, the dose can be increased or reduced depending on the age, weight, condition of the patient, severity of the disease or type of administration.

EXAMPLES

The designation of the ligands has been carried according to the IUPAC nomenclature with the program ACD/name, version 12.01 according to Advanced Chemistry Development Inc.

ABBREVIATIONS

| s | singlet | t | triplet |
|---|---|---|---|
| d | doublet | q | quartet |
| dd | double doublet | m | multiplet (broad/superimposed) |
| L | ligand | | |

Starting Compounds

A. Pyrimidine-2-ol-1-oxide hydrochloride

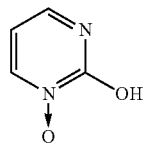

0.261 mol (19.85 g) hydroxy urea have been dissolved in 390 ml 1 M HCl and 0.235 mol (51.77 g) 1,1,3,3-tetraethoxypropane were added dropwise under ice cooling, with the internal temperature being maintained at 1-2° C. The solution was thawed in an ice bath to room temperature and stirred over night, then evaporated to dryness. The residue was suspended with 250 ml of acetone, the mixture was cooled in an ice/ethanol bath, the solid filtered off and washed with a little ice-cold acetone. After drying, 24.5 g of crude product were obtained. The crude product was recrystallized with 460 ml of methanol from the boiling heat, cooled in an ice/ethanol bath, filtered off and dried. The mother liquor was concentrated on a rotary evaporator until again product started to precipitate, then a second fraction was crystallized similarly. After drying 11.8 g (1. fraction) and 5.9 g (2. fraction) the title compound were obtained.

IR (in substance, cm$^{-1}$): 3114, 3082, 2995, 2935, 2837, 2776, 2718, 2467, 1734, 1575, 1492, 1421, 1363, 1314, 1232, 1176, 1123, 1100, 1073, 911, 861, 773, 733, 689, 574 (2. fraction).

CN-elementary analysis: C, 32.29; N, 18.98 (1. fraction); C, 32.41; N, 18.98 (2. fraction).

Chloride content: 24.6% (m/m) (1. fraction), 23.6% (m/m) (2. fraction) LC-MS: 113 (M+H).

1H-NMR (DMSO-d$_6$, 400 MHz). δ [ppm]=9.05 (dd, 1H), 8.55 (dd, 1H), 6.74 (t, 1H).

B. 4-Methylpyrimidine-2-ol-1-oxid hydrochloride

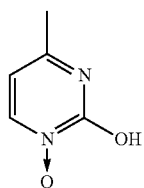

0.10 mol (7.61 g) hydroxy urea were dissolved in 150 ml of 1 M HCl and 0.11 mol (16.15 g, techn. 90%) of 4,4,-dimethoxy-2-butanone was added dropwise under ice cooling whereby the internal temperature was maintained at 1-3° C. The solution was thawed in an ice bath to room temperature and stirred over night, then filtered and evaporated to dryness. The residue was suspended with 100 ml of acetone, the mixture was cooled to −18° C., the solid filtered off and washed with a little ice-cold acetone. After drying, 10.7 g or crude product were obtained. The crude product was recrystallized with 1750 ml ethanol from the boiling heat, cooled in an ice/ethanol bath, filtered off, washed with a little ethanol and dried (fraction 1). The mother liquor was concentrated on a rotary evaporator until again product started to precipitate, cool stored and a second fraction isolated. After drying, 6.15 g (1. fraction) and 1.86 g (2. fraction) product was obtained. Both fractions were combined and recrystallized from the boiling heat with 230 ml 90% ethanol (10 (D/0 water) similarly. After drying, 3.75 g (3. fraction) and 2.36 g (4. fraction) of the title compound were obtained.

IR (in substance, cm$^{-1}$): 3102, 3034, 2926, 2841, 2730, 2657, 2531, 1741, 1650, 1602, 1581, 1518, 1456, 1374, 1302, 1184, 1131, 1110, 1037, 977, 888, 821, 780, 734, 697, 603 (3. fraction).

CHN-elementary analysis: C, 37.48; H, 4.33; N, 17.12 (3. Fraction); C, 37.12; H, 4.30; N, 17.08 (4. fraction).

LC-MS: 127 (M+H).

1H-NMR (DMSO-d$_6$, 400 MHz): δ [ppm]=8.97 (d, 1H), 6.73 (d, 1H), 2.49 (s, 3H).

C. 4,6-Dimethylpyrimidine-2-ol-1-oxide hydrochloride

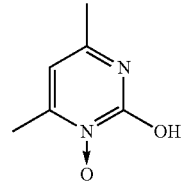

0.40 mol (30.6 g) hydroxy urea was dissolved in 600 ml of 1 M HCl and 0.50 mol (50.06 g) acetyl acetone were added dropwise under ice cooling, maintaining the internal temperature at 1-3° C. The solution was thawed to room temperature in an ice bath and stirred over night, then filtered off and evaporated to dryness. The residue was suspended with 400 ml of acetone, the mixture was cooled to −18° C., the solid filtered off and washed with a little ice-cold acetone. After drying, 45.5 g of crude product were obtained. The crude product was recrystallized with 4.0 l ethanol from the boiling heat, cooled to −18° C., filtered off and washed with little ethanol and dried (fraction 1). The mother liquor was concentrated on a rotary evaporator until product started to precipitate again, cool stored and a second fraction isolated. After drying 26.0 g (1. fraction, purity>98%) and 11.0 g (2. fraction, contained 32% NH$_4$Cl as by-product) of the title compound was obtained.

IR (in substance, cm$^{-1}$): 3077, 3052, 2938, 2855, 2796, 2521, 1740, 1610, 1564, 1509, 1423, 1368, 1316, 1215, 1163, 1141, 1089, 1049, 1026, 997, 975, 852, 775, 741, 695, 626, 601 (1. fraction).

CHN-elementary analysis: C, 40.74; H, 5.03; N, 15.78 (1. fraction); C, 27.75; H, 5.87; N, 18.98 (2. fraction).

Chloride content: 19.9% (m/m) (1. fraction), 33.4% (m/m) (2. fraction) LC-MS: 141 (M+H).

1H-NMR (DMSO-d$_6$, 400 MHz): δ [ppm]=6.78 (s, 1H); 2.53 (s, 3H); 2.43 (s, 3H) (1. fraction).

D. 4,6-Diethylpyrimidine-2-ol 1-oxid hydrochloride

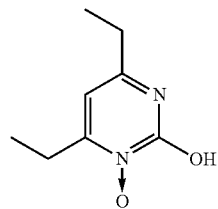

0.19 mol (14.45 g) hydroxy urea were dissolved in 300 ml 1 M HCl, 300 ml of methanol was added and 0.19 mol (24.35 g) of 3,5-heptandione was added dropwise under ice cooling, maintaining the internal temperature at 1-2° C. The solution was thawed to room temperature in an ice bath and stirred over night, then evaporated to dryness. The residue was suspended with 200 ml of acetone, the mixture was cooled to below 0° C. in an ice/ethanol bath, the solid filtered off and washed with a little ice-cold acetone. After drying, 7.88 g of a product was obtained which contained 48% of the title compound and 52% ammonium chloride as by-product.

IR (in substance, cm$^{-1}$): 3116, 3024, 2804, 2687, 2628, 1996, 1746, 1603, 1572, 1512, 1443, 1394, 1297, 1213, 1156, 1082, 1061, 963, 901, 861, 814, 745, 700.

CHN-elementary analysis: C, 22.71; H, 6.94; N, 19.99.
Chloride content: 42.9% (m/m)
LC-MS: 169 (M+H).
1H-NMR (DMSO-d$_6$, 400 MHz): δ [ppm]=6.75 (s, 1H), 2.86 (q, 2H), 2.70 (q, 2H), 1.21 (t, 3H), 1.20 (t, 3H).

E. 4-Methyl-6-(2-methylpropyl)pyrimidine-2-ol-1-oxide hydrochloride

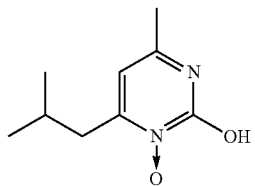

0.20 mol (15.21 g) hydroxy urea were dissolved in 300 ml of M HCl, 300 ml of methanol were added, and 0.20 mol (28.44 g) 6-methyl-2,4-heptanedione were added dropwise while cooling at −12 to −10° C. The solution was allowed to warm slowly to room temperature and stirred over night, then evaporated to dryness. The residue was suspended with 200 ml of acetone, the mixture cooled to below 0° C. in an ice/ethanol bath, the solid filtered off and washed with a little ice-cold acetone. After drying 7.23 g of a product was obtained, which contained 58% of the title compound and 42% of the by-product ammonium chloride.

IR (in substance, cm$^{-1}$): 3106, 3011, 2963, 2576, 1834, 1740, 1604, 1567, 1514, 1467, 1446, 1403, 1371, 1321, 1280, 1234, 1209, 1149, 1104, 1070, 1032, 1010, 915, 861, 820, 774, 750, 712, 680, 644, 615, 580.

CHN-elementary analysis: C, 28.68; H, 6.93; N, 18.33.
Chloride content: 37.6% (m/m)
LC-MS: 183 (M+H).
1H-NMR (DMSO-d$_6$, 400 MHz): δ [ppm]=6.76 (s, 1H), 2.72 (d, 2H), 2.44 (s, 3H), 2.13 (m, 1H), 0.91 (d, 6H). From the NMR-spectrum was estimated that the product contained approximately 2% of the regioisomere 6-methyl-4-(2-methylpropyl)pyrimidine-2-ol-1-oxide hydrochloride.

F. 4,5,6-Trimethylpyrimidine-2-ol-1-oxide hydrochloride

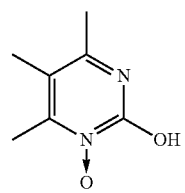

0.263 mol (20.0 g) hydroxy urea were dissolved in 263 ml 1 M HCl and 0.876 mol (100 g) 3-methyl-2,4-pentanedione (95%, Alfa Aesar) were added dropwise under ice cooling. The two-phase-mixture was stirred for 1 h at room temperature, and then it was extracted twice with 530 ml ethyl acetate. The combined organic phases were dried with sodium sulphate and concentrated on a rotary evaporator to dryness. 86.6 g 3-methyl-2,4-pentanedione, depleted with acetyl acetone, were obtained.

0.758 mol (60.84 g) hydroxy urea were dissolved in 500 ml of 2 M HCl and 200 ml of methanol and 0.758 mol (86.56 g) 3-methyl-2,4-pentanedione were added. The solution was stirred for 1 h at 50° C., and then concentrated to dryness. The residue was suspended in 80 ml of acetone, the mixture was cooled to below 0° C. in an ice/ethanol bath, the solid filtered off, washed with a little ice-cold acetone and dried. 21.7 g of intermediate product were heated to boiling in 150 ml methanol, hot filtered from insoluble fractions and again evaporated to dryness. There were obtained 7.05 g solid (1. fraction) which contained 9.6% of the title compound and 90% of the by-product ammonium chloride.

From the acetone mother liquor further solid precipitated which was filtered off, washed with a little acetone and dried. 2.50 g of the solid (2. fraction) contained 82% of the title compound and 18% of the by-product ammonium chloride.

IR (in substance, cm$^{-1}$): 3112, 2997, 2934, 2850, 2796, 2629, 2544, 1734, 1612, 1582, 1513, 1472, 1392, 1373, 1309, 1247, 1215, 1152, 1132, 1093, 1014, 945, 896, 803, 777, 742, 707, 630, 603, 558, 528, 500.

CHN-elementary analysis: C, 36.31; H, 6.16; N, 16.28 (2. fraction).
Chloride content: 25.9% (m/m) (2. fraction)
LC-MS: 155 (M+H).
1H-NMR (DMSO-d$_6$, 400 MHz): δ [ppm]=2.56 (s, 3H), 2.47 (s, 3H), 2.05 (s, 3H). From the NMR-spectrum was estimated that the product contained approximately 9% 4,6-dimethylpyrimidine-2-ol-1-oxide hydrochloride as by-product.

G. 5-Chloro-4,6-dimethylpyrimidine-2-ol-1-oxide hydrochloride

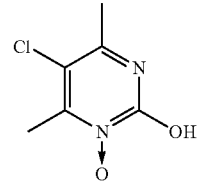

0.20 mol (15.21 g) hydroxy urea were dissolved in 300 ml of 1 M HCl, 300 ml methanol were added and 0.20 mol (26.91 g) of 3-chloro-2,4-pentandedione were added dropwise under ice cooling at 1-2° C. The two-phase-mixture was allowed to warm slowly to room temperature and stirred over night. The clear solution was then evaporated to dryness. The residue was suspended with 200 ml of acetone, the mixture was cooled to below 0° C. in an ice/ethanol bath, the solid filtered off and washed with a little ice-cold acetone. The filtrate was concentrated to dryness, the residue was suspended in 20 ml of tetrahydrofuran, filtered off, washed with little Tetrahydrofuran and dried. 1.40 g of a product containing about 53% of the title compound and 47% of the by-product ammonium chloride were obtained.

IR (in substance, cm$^{-1}$): 3115, 2900, 2667, 2516, 1745, 1577, 1505, 1378, 1310, 1194, 1135, 1102, 1049, 973, 900, 835, 737, 674, 578.
Chloride content: 40.1% (m/m)
LC-MS: 175 (M+H).

1H-NMR (DMSO-d$_6$, 400 MHz): δ [ppm]=2.49 (s, 3H), 2.37 (s, 3H).

H. 4-Ethylpyrimidine-2-ol-1-oxide hydrochloride

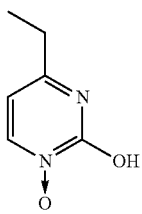

1,1-Dimethoxypentan-3-on (T. Harayama, H. Cho and Y. Inubushi, Chem. Pharm. Bull. 1978, 26, 1201-1214)

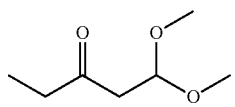

In a multi-neck flask with internal thermometer and KPG-stirrer 0.96 mol (89 g) propionic acid chloride were charged and cooled with a salt/ice freezing mixture. 0.82 mol (110 g) aluminium chloride was added portion wise and the mixture was stirred vigorously for 10 min and mixed with 50 ml of chloroform. Then, within about 1 h 0.93 mol (100 g) vinyl bromide was added in small portions (maximum internal temperature 14° C.). The mixture was stirred on ice for 1 h, and then the reaction mixture was poured onto 500 g ice and extracted several times with a total of 1 l of chloroform. The combined organic phases were washed 4 times with 1 l of water, dried with sodium sulphate and the chloroform was distilled off on a rotary evaporator. The residue was distilled in a rotary evaporator at 80° C. water bath temperature and 16 mbar (head temperature about 47° C.), which resulted in 118 g intermediate product (unstable, storage −18° C.).

118 g intermediate product were dissolved in 600 ml anhydrous methanol and cooled on ice. 1.03 mol (55.65 g) natrium methoxid were dissolved in 360 ml anhydrous methanol and added dropwise within 30 min and the mixture was stirred at room temperature for further 18 h. The resulting salt was filtered off, washed with a small amount of dry methanol and the filtrate was concentrated on a rotary evaporator. The residue was distilled at a rotary evaporator at a water bath temperature of 75° C. and 4 mbar (head temperature 40-52° C.). 61.4 g of a product mixture containing 62% (m/m) of the title compound (corresponding to 38 g) were obtained.

1H-NMR (DMSO-d$_6$, 400 MHz): δ [ppm]=4.74 (t, 1H), 3.23 (s, 6H), 2.70 (d, 2H), 2.45 (q, 2H), 0.90 (t, 3H) (title compound, 62% m/m in product mixture); δ=7.69 (d, 1H), 5.61 (d, 1H), 3.69 (s, 3H), 2.48 (q, 2H), 0.96 (t, 3H) ((1E)-1-methoxypent-1-en-3-on, 38% in product mixture).

4-Ethylpyrimidin-2-ol-1-oxide hydrochloride 0.388 mol (25.9 g) hydroxy urea were dissolved in 195 ml 2 M HCl, 80 ml of methanol were added and 0.388 mol (56.7 g) of 1,1-dimethoxypentane-3-on (62% content in product mixture) were added dropwise under cooling with the internal temperature being maintained at −6 to −7° C. The solution was thawed to room temperature in an ice bath and stirred for 1 h, then evaporated until dryness. The residue was suspended with 100 ml of acetone, the mixture was cooled to below 0° C. in an ice/ethanol bath, the solid filtered off and washed with little ice-cold acetone. After drying 32.6 g crude product were obtained. The crude product was heated until boiling with 200 ml ethanol, hot filtered and slowly cooled to −18° C. The precipitated solid was filtered off, washed with a little amount of ethanol and dried. 11.7 g of the title compound were obtained.

IR (in substance, cm$^{-1}$): 3115, 3038, 2936, 2678, 2518, 1753, 1606, 1585, 1516, 1465, 1403, 1381, 1301, 1229, 1184, 1134, 1109, 1053, 1002, 896, 803, 769, 736, 680, 605, 540, 513, 494, 474.

CHN-elementary analysis: C, 40.72; H, 5.03; N, 15.32.

LC-MS: 141 (M+H).

1H-NMR (DMSO-d$_6$, 400 MHz): δ [ppm]=8.92 (d, 1H), 6.70 (d, 1H), 2.73 (q, 2H); 1.19 (t, 3H). From the NMR-spectrum was estimated that the product contained <3% of the regioisomere 6-ethylpyrimidine-2-ol-1-oxide hydrochloride.

I. 6-Ethyl-4-methylpyrimidine-2-ol-1-oxide hydrochloride

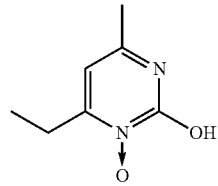

0.12 mol (9.13 g) hydroxy urea were dissolved in 50 ml 2 M HCl, 20 ml of methanol were added and 0.10 mol (11.41 g) 2,4-hexanedione were added dropwise under cooling by approximately −15° C. Further 30 ml of water and 10 ml of methanol were added. The two-phase reaction mixture was allowed to warm up slowly to room temperature and was stirred at room temperature for further 2 h, then evaporated until dryness. The residue was suspended with 50 ml of acetone, the mixture was cooled in an ice/ethanol bath, the solid filtered off and washed with a little ice-cold acetone. After drying 7.88 g crude product were obtained which were recrystallized from 45 ml ethanol wherefrom first an insoluble salt compound was hot filtered off and the product was subsequently recrystallized from the filtrate at −18° C. 3.0 g product were obtained which were again recrystallized from 28 ml ethanol. Finally 2.26 g of the title compound were obtained.

IR (in substance, cm$^{-1}$): 3093, 2997, 2945, 2679, 2555, 1805, 1741, 1601, 1571, 1508, 1435, 1401, 1370, 1327, 1290, 1253, 1213, 1157, 1103, 1049, 903, 849, 811, 766, 742, 701, 669, 626, 607, 582, 512, 494.

LC-MS (m/z): 155.7 (M+H).

1H-NMR (DMSO-d$_6$, 400 MHz): δ [ppm]=6.78 (s, 1H), 2.88 (q, 2H), 2.46 (s, 3H), 1.21 (t, 3H). From the NMR-spectrum was estimated that the product contained approximately 6.6% of the regioisomer 4-ethyl-6-methylpyrimidine-2-ol-1-oxide hydrochloride.

J. 4-Methyl-6,7-dihydro-5H-cyclopenta[d]pyrimidine-2-ol-1-oxide hydrochloride

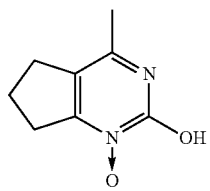

0.20 mol (15.21 g) hydroxy urea was dissolved in 200 ml of 1 M HCl, 200 ml of methanol were added and 0.20 mol (25.23 g) 2-acetylcyclopentanone were added dropwise, 1 further hour stirred and then the solution was evaporated at the rotary evaporator until dryness. The residue was suspended with 100 ml of acetone, the solid filtered off and washed with acetone. After drying 12.41 g crude product 1 were obtained which were solubilised in the boiling heat with 1200 ml isopropanol and hot filtered. The filtrate was evaporated until dryness and 8.49 g crude product 2 were obtained. This was solubilised in the boiling heat in 200 ml of ethanol and 200 ml of tetrahydrofuran were added. The precipitated solid was filtered off and dried. 5.63 g of a product were obtained which contained 91.5% of the title compound and 8.5% ammonium chloride.

IR (in substance, cm$^{-1}$): 3133, 3042, 2841, 2751, 2480, 1730, 1613, 1590, 1493, 1404, 1374, 1314, 1289, 1221, 1134, 1062, 1044, 1020, 972, 938, 894, 868, 822, 740, 707, 637, 575, 552, 525, 509.

LC-MS (m/z): 167.5 (M+H).

CHN-elementary analysis: C, 43.93; H, 6.07; N, 13.41.

Chloride content: 21.7% (m/m)

1H-NMR (DMSO-d$_6$, 400 MHz): δ [ppm]=3.22 (t, 2H), 2.82 (t, 2H), 2.42 (s, 3H), 2.13 (quintett, 2H). From the MNR-spectrum was estimated that the product contained approximately 6% of the regioisomere 4-methyl-6,7-dihydro-5H-cyclopenta[d]pyrimidine-2-ol-3-oxide hydrochloride.

K. 4-Methyl-5,6,7,8-tetrahydrochinazoline-2-ol-3-oxide hydrochloride

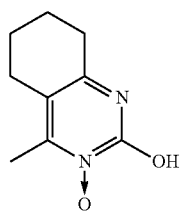

0.08 mol (6.08 g) hydroxy urea were dissolved in 40 ml of 2 M HCl, 40 ml of methanol were added and 0.08 mol (11.21 g) 2-acetylcyclohexanone were added dropwise under cooling at approximately −15° C., stirred one further hour and thereby warmed up to 20° C. This was carried out six times in total. The combined reaction mixtures were then evaporated at the rotary evaporator. The residue was suspended with acetone, the solid filtered off and washed with acetone. After drying 36.97 g crude product 1 were obtained which were suspended with 250 ml ethanol and hot filtered. The filtrate was evaporated until dryness and 20.87 g crude product 2 were obtained. This was solubilised in the boiling heat in 500 ml of ethanol, hot filtered, and the filtrate was combined with 800 ml tetrahydrofuran. The precipitated solid was filtered off and dried. 14.3 g of a product were obtained which contained 87% of the title compound and 13% ammonium chloride.

IR (in substance, cm$^{-1}$): 3135, 3044, 2937, 2875, 2805, 2706, 2426, 1743, 1572, 1501, 1443, 1403, 1345, 1288, 1260, 1235, 1150, 1122, 1086, 1041, 908, 883, 824, 740, 707, 669, 643, 605, 546, 514.

CHN-elementary analysis: C, 43.63; H, 6.08; N, 14.66.

Chloride content: 22.2% (m/m)

1H-NMR (DMSO-d$_6$, 400 MHz): δ [ppm]=2.76 (m, 2H), 2.53 (s, 3H), 2.49 (m, 2H), 1.70 (m, 4H). From the NMR-spectrum was estimated that the product contained approximately 5% of the regioisomere 4-methyl-5,6,7,8-tetrahydrochinazolin-2-ol-1-oxide hydrochloride.

L. 4-(Propan-2-yl)pyrimidine-2-ol-1-oxide hydrochloride

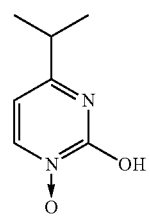

0.187 mol (14.22 g) hydroxy urea were dissolved in 200 ml of 1 M HCl and 0.187 mol (30 g) 1,1-dimethoxy-4-methyl-pentane-3-on (E. E. Royals and K. C. Brannock, J. Am Chem. Soc. 1953, 75, 2050-2053) were added dropwise under cooling, with the internal temperature being maintained at 0-1° C. The two-phase mixture was thawed to room temperature in an ice bath and stirred for 12 h, then evaporated until dryness. The residue was suspended with 100 ml acetone, the mixture was cooled in an ice/ethanol bath, the solid filtered off and washed with a little ice-cold acetone. After drying 15.79 g crude product 1 were obtained. 11.04 g of crude product 1 were heated until boiling with 141 ml ethanol and precipitated solid was filtered off after cooling. The filtrate was again evaporated until dryness and 8.49 g crude product 2 were obtained which were heated until boiling in 80 ml ethanol and hot filtered. The filtrate was cooled down slowly to room temperature and over night down to −18° C. The precipitated solid was filtered off and after drying 2.18 g of the title compound were obtained.

IR (in substance, cm$^{-1}$): 2971, 2585, 1815, 1748, 1598, 1572, 1513, 1463, 1390, 1305, 1230, 1186, 1163, 1132, 1049, 986, 934, 901, 815, 773, 749, 719, 681, 616, 582, 518, 498, 484, 478.

CHN-elementary analysis: C, 43.54; H, 6.10; N, 14.50

LC-MS (m/z): 155.5 (M+H).

1H-NMR (DMSO-d$_6$, 400 MHz): δ [ppm]=8.88 (d, 1H), 6.68 (d, 1H), 3.02 (heptett, 1H); 1.20 (d, 6H)

M. 4-Ethyl-6-methylpyrimidine-2-ol 1-oxide hydrochloride

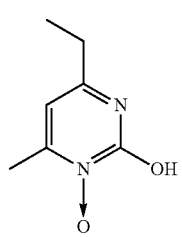

Various mother liquors from recrystallization from the synthesis of the regioisomer 6-ethyl-4-methyl-pyrimidine-2-ol 1-oxide hydrochloride (Example I) were combined and evaporated to dryness. In total 22.14 grams of this product mixture, containing about 50% of the title compound, were heated in 140 ml of ethanol to boiling, filtered hot and evaporated to dryness. 20.96 g of the residue was recrystallized from 90 ml of ethanol, in doing so first 0.82 g of an insoluble fraction were separated in the heat, and then it was slowly cooled down from the boiling point to −18° C. 17.25 g of a precipitate were then recrystallized accordingly from 150 ml of ethanol/70 ml of tetrahydrofuran, whereby 6.05 g of a solid predominantly containing 6-ethyl-4-methyl-pyrimidine-2-ol 1-oxide hydrochloride was separated. The filtrate was concentrated to dryness and 9.53 g of the residue were recrystallized from 180 ml of isopropanol. 7.57 g of a product mixture were obtained (63% enrichment) and recrystallized several times from isopropanol in a corresponding manner. Finally there were obtained 0.69 g of the title compound.

IR (neat, cm$^{-1}$): 3077, 2853, 2685, 2550, 1745, 1608, 1568, 1514, 1461, 1416, 1370, 1323, 1304, 1249, 1211, 1160, 1142, 1104, 1069, 1028, 994, 936, 887, 849, 767, 746, 707, 685, 625, 599, 567, 525, 500.

LC-MS (m/z): 155 (M+H).

1H-NMR (DMSO-d$_6$, 400 MHz): δ [ppm]=6.83 (s, 1H), 2.70 (q, 2H), 2.55 (s, 3H), 1.20 (t, 3H). From the NMR spectrum it was estimated that the product contained approximately 13% of the regioisomer 6-ethyl-4-methyl-pyrimidin-2-ol 1-oxide hydrochloride.

N. 4-tert-Butylpyrimidine-2-ol 1-oxide hydrochloride

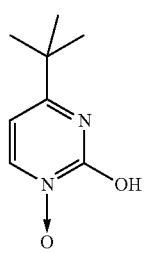

The synthesis of the precursor 1,1-dimethoxy-4,4-dimethylpentane-3-one was performed in analogy to E. E. Royals and K. C. Brannock (J. Am. Chem Soc. 1953, 75, 2050-2053), wherein a mixture of about 20% of the desired precursor and 80% of the byproduct 1-methoxy-4,4-dimethylpent-1-en-3-one was obtained. To 32.8 g of this mixture were added 33.9 mmol (5.63 g) N-benzyloxy urea, 51 ml of methanol, 1.7 ml of water and 4.06 ml of sulfuric acid (analogous to M. Yamaguchi et al., J. Inorg. Biochemistry 2006, 100, 260-269). It was stirred at room temperature with portionwise addition of in total 153 mmol (25 g) N-benzyloxy urea for 5 h, until N-benzyloxy urea could be detected in the reaction mixture (TLC hexane/ethyl acetate 2/1, 1% acetic acid). The reaction mixture was evaporated to dryness, the residue taken up in water/dichloromethane, the aqueous phase was adjusted to pH 9.3 with saturated sodium carbonate solution and extracted three times with dichloromethane. The combined organic phases were washed with water, dried over sodium sulfate and evaporated to dryness. 51.8 g of a crude product were obtained which was chromatographed with cyclohexane/ethyl acetate over silica gel. 46.4 mmol (12.0 g) purified intermediate product were obtained, which was dissolved in 240 ml of methanol and hydrogenated with 0.93 g of 10% Pd/C for 3.5 h with hydrogen. It was filtered over Celite, the filtrate was added with 50 ml of 1 M HCl and evaporated to dryness. The crude product was suspended in 100 ml of water, filtered off from insoluble constituents and the filtrate was concentrated. After drying, 8.15 g (39.8 mmol, 5.0% yield over three steps) of the title compound were obtained.

IR (neat, cm$^{-1}$): 2850, 2482, 1758, 1605, 1565, 1517, 1494, 1467, 1389, 1377, 1310, 1264, 1190, 1118, 1086, 887, 828, 751, 730, 703

1H-NMR (DMSO-d$_6$, 400 MHz): δ [ppm]=8.66 (d, 1H), 6.61 (d, 1H), 1.27 (s, 9H)

O. 5,6-Dimethylpyrimidine-2-ol 1-oxide hydrochloride

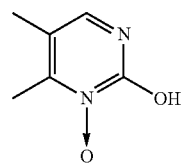

The synthesis of the precursor 4,4-dimethoxy-3-methylbutan-2-one was performed in analogy to E. E. Royals and K. C. Brannock (J. Am. Chem., 1953, 75, 2050-2053) and yielded a mixture of 58% of the desired precursor, 24% of the byproduct 1,1-dimethoxy-pentan-3-one and about 18% elimination product. 102 g of this mixture (0.405 mol of 4,4-dimethoxy-3-methylbutan-2-one) were dissolved in 30 ml of methanol and added dropwise to 0.698 mol of N-hydroxyurea in 400 ml of 2M HCl, while the internal temperature was maintained at −10 to −4° C. The solution was thawed to room temperature, stirred for 1 h, and then evaporated to dryness. The residue was slurried with 200 ml of acetone, the solid filtered off and washed with little ice-cold acetone. After drying, the crude product was heated with 150 ml of ethanol to boiling, filtered hot, concentrated to 50 ml and cooled to −18° C. The precipitated solid was filtered off, washed with little ethanol and dried. 20 g of this solid was again recrystallized from 100 ml of ethanol, and finally 10 g (12% yield) of the title compound were obtained (content of 85% the title compound and 13% ammonium chloride).

IR (neat, cm$^{-1}$): 2569, 2539, 1726, 1628, 1589, 1503, 1453, 1378, 1336, 1255, 1220, 1157, 1141, 1120, 1021, 919, 828, 755, 734, 713

1H-NMR (DMSO-d$_6$, 400 MHz): δ [ppm]=8.98 (s, 1H); 2.50 (s, 3H); 2.08 (s, 3H)

P. 6-n-Propylpyrimidine-2-ol 1-oxide hydrochloride

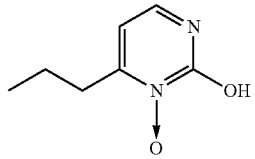

The synthesis of the precursor 1,1-dimethoxyhexane-3-one was performed in analogy to E. E. Royals and K. C. Brannock (J. Am. Chem. Soc. 1953, 75, 2050-2053) and yielded a mixture of 75% of the desired precursor, 13% of the byproduct 3-(dimethoxymethyl) pentan-2-one and about 12% of elimination products. 29.2 g of this mixture (0.137 mol 1,1-dimethoxyhexane-3-one) were mixed with 0.164 moles (27.3 g) N-benzyloxy urea, added with 150 ml of methanol and 20 ml of sulfuric acid (analogous to M. Yamaguchi et al., J. Inorg. Biochemistry 2006, 100, 260-269). The mixture was stirred at room temperature, then further 0.0164 mmol (2.73 g) of N-benzyloxy urea were added and it was heated for 1 h at 50° C. The mixture was evaporated to dryness, the residue was taken up in water/dichloromethane, the aqueous phase was adjusted to pH 11 with saturated sodium carbonate solution and extracted three times with dichloromethane. The combined organic phases were washed with water, dried over magnesium sulfate and evaporated to dryness. There were obtained 40.3 g of a crude product which was chromatographed with cyclohexane/ethyl acetate over silica gel. 0.026 mol (6.3 g) of the purified intermediate were dissolved in 100 ml of methanol and hydrogenated with 0.53 g of 10% Pd/C for 0.5 h with hydrogen. It was filtered off through Celite, the filtrate was concentrated to 50 ml added with 50 ml of 1 M HCl and evaporated to dryness. The crude product was recrystallized from 50 ml of 2-propanol and 200 ml of diethyl ether. 3.46 g (18.2 mmol, 13% yield over 2 steps) of the title compound were obtained.

IR (neat, cm$^{-1}$): 2591, 2536, 2477, 1770, 1736, 1608, 1580, 1311, 1194, 1185, 1130, 1115, 1082, 1001, 904, 892, 823, 787, 736, 680

1H-NMR (DMSO-d$_6$, 400 MHz): δ [ppm]=8.98 (d, 1H), 6.75 (d, 1H), 2.74 (t, 2H), 1.69 (hextett, 2H), 0.93 (t, 3H)

IRON COMPLEX COMPOUNDS

Examples

Example 1

Tris-(pyrimidine-2-ol-1-oxide)-iron(III) complex

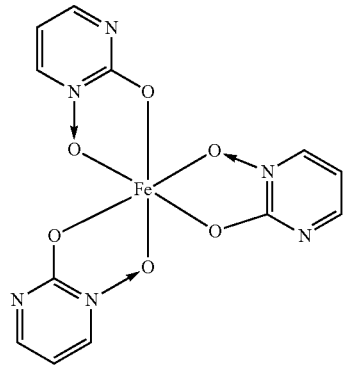

114 mmol (16.93 g) pyrimidine-2-ol-1-oxide hydrochloride were dissolved in 150 ml of water and 38 mmol (10.27 g) FeCl$_3$*6H$_2$O dissolved in 15 ml water were added. The solution was adjusted to pH 6.3 with approximately 90 ml 2 M NaOH and stirred for 0.5 h. The product was filtered off, washed with water and dried in a vacuum drying oven at 50° C. 14.2 g of the title compound were obtained.

IR (in substance, cm$^{-1}$): 3082, 3054, 1596, 1506, 1431, 1366, 1278, 1197, 1136, 1108, 1055, 907, 798, 765, 613, 554, 513.

CHN-elementary analysis: C, 35.77; H, 2.78; N, 20.23.

ESI-MS: 278.3 (FeL$_2^+$); 390.4 (M+H$^+$); 412.4 (M+Na$^+$).

Fe-content: 13.61% [m/m]

Example 2

Tris-(4-methylpyrimidine-2-ol-oxide)-iron(III) complex

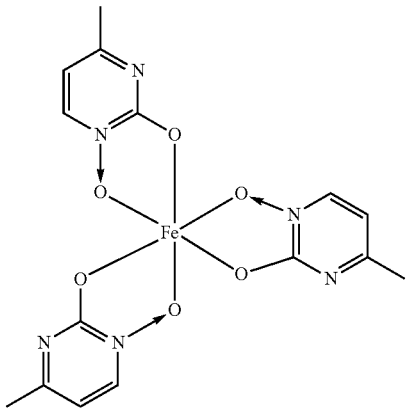

21 mmol (3.76 g, approximately 90% purity) 4-methylpyrimidine-2-ol-1-oxide hydrochloride were dissolved in 15 ml water and 7.0 mmol (1.89 g) FeCl$_3$*6H$_2$O dissolved in 5 ml water were added. The solution was adjusted to pH 5.85 with approximately 44 ml 1 M NaOH and stirred for 0.5 h. The product was filtered off, washed with water and dried in a vacuum drying oven at 50° C. 3.03 g of the title compound were obtained.

IR (in substance, cm$^{-1}$): 3400, 3074, 1602, 1545, 1503, 1425, 1378, 1339, 1249, 1201, 1145, 1110, 1032, 954, 805, 762, 645, 600.

CHN-elementary analysis: C, 38.42; H, 4.10; N, 18.11.

ESI-MS: 306.4 (FeL$_2^+$); 432.4 (M+H$^+$).

Fe-content: 12.15% [m/m]

Example 3

Tris-(4,6-dimethylpyrimidine-2-ol-1-oxide)-iron(III) complex

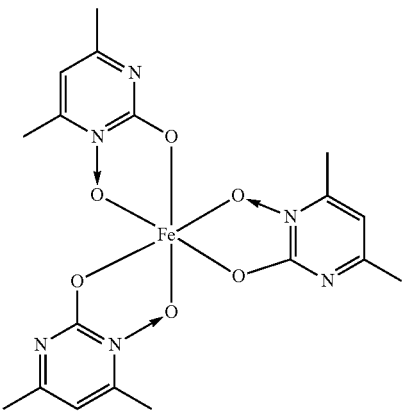

120 mmol (21.19 g) 4,6-dimethylpyrimidine-2-ol-1-oxide hydrochloride were dissolved in 15 ml of water and 40 mmol (10.81 g) $FeCl_3*6H_2O$ dissolved in 10 ml water were added. The solution was adjusted to pH 5.90 with approximately 238 ml 1 M NaOH and stirred for 0.5 h. The product was filtered off, washed with water and dried in a vacuum drying oven at 50° C. 18.66 g of the title compound were obtained.

IR (in substance, $cm^{-1}$): 3596, 3441, 3077, 1604, 1551, 1511, 1441, 1393, 1380, 1360, 1320, 1153, 1097, 1029, 875, 856, 798, 651, 564, 524, 486.

CHN-elementary analysis: C, 44.27; H, 4.22; N, 17.35.

ESI-MS: 334.4 ($FeL_2^+$); 474.5 ($M+H^+$); 496.6 ($M+Na^+$).

Fe-content: 11.33% [m/m]

No melting point, at about 230° C. exothermic decomposition starts.

Example 4

Tris-(4,6-diethylpyrimidine-2-ol-1-oxide)-iron(III) complex

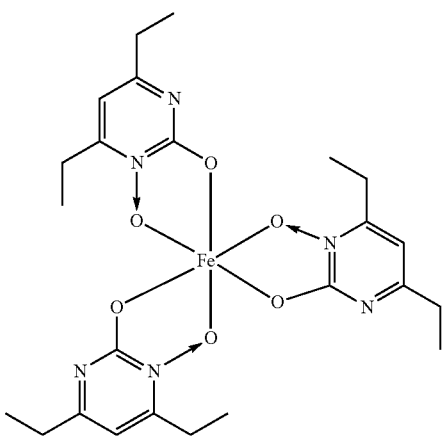

14 mmol (6.1 g, approximately 48% purity, 52% ammonium chloride) 4,6-diethylpyrimidine-2-ol-1-oxide hydrochloride were dissolved in 15 ml water and 4.67 mmol (1.26 g) $FeCl_3*6H_2O$ dissolved in 2 ml water were added. The solution was adjusted to pH 5.85 with 27.7 ml 1 M NaOH and stirred for 0.5 h. The product was filtered off, washed with water and dried at 50° C. in a vacuum drying oven. 2.57 g of the title compound were obtained.

IR (in substance, $cm^{-1}$): 3593, 3378, 3087, 2969, 2934, 2880, 1602, 1549, 1510, 1460, 1406, 1328, 1255, 1235, 1146, 1108, 1073, 1027, 964, 903, 863, 807, 764, 701, 672, 645, 619, 578, 522.

CHN-elementary analysis: C, 49.23; H, 6.03; N, 14.43.

Fe-content: 10.05% [m/m]

Example 5

Tris-(4-methyl-6-(2-methylpropyl)pyrimidin-2-ol-1-oxide)-iron(III) complex

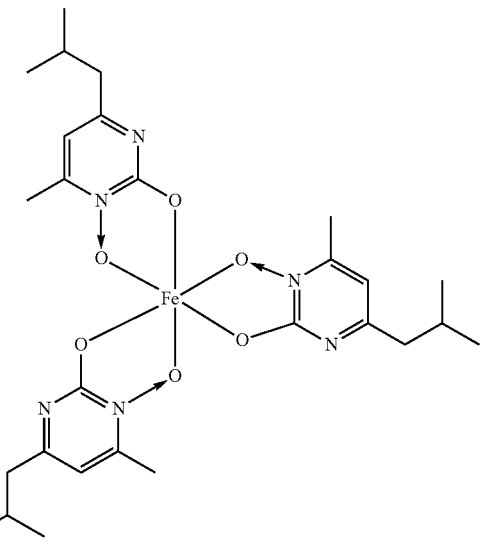

15 mmol (5.74 g, approximately 58% purity, 42% ammonium chloride) 4-methyl-6-(2-methylpropyl)pyrimidine-2-ol-1-oxide hydrochloride were dissolved in 25 ml water and 5.0 mmol (1.35 g) $FeCl_3*6H_2O$ dissolved in 2 ml water were added. The solution was adjusted to pH 5.88 with 29.2 ml 1 M NaOH and stirred for 0.5 h. The product was filtered off, washed with water and dried in a vacuum drying oven at 50° C. There was obtained 3.00 of the title compound.

IR (in substance, $cm^{-1}$): 2959, 2929, 2872, 1598, 1549, 1513, 1462, 1434, 1400, 1355, 1289, 1233, 1151, 1122, 1102, 1034, 990, 928, 879, 853, 799, 769, 701, 648, 606, 575.

CHN-elementary analysis: C, 53.71; H, 6.40; N, 13.92.

Fe-content: 9.29% [m/m]

Example 6

Tris-(4,5,6-trimethylpyrimidine-2-ol-1-oxide)-iron(III) complex

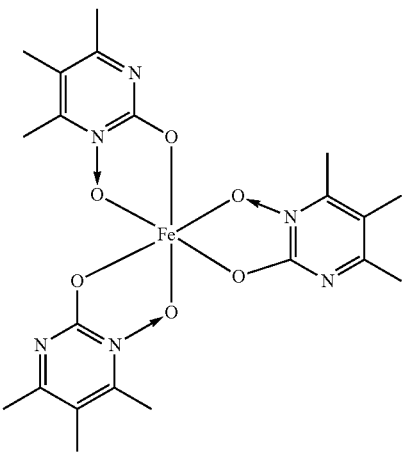

10.2 mmol (2.38 g, approximately 82% purity, 18% ammonium chloride) 4,5,6-trimethylpyrimidine-2-ol-1-oxide hydrochloride were dissolved in 5 ml water and 3.4 mmol (0.93 g) $FeCl_3 \cdot 6H_2O$ dissolved in 1 ml water were added. The solution was adjusted to pH 6.04 with 19 ml 1 M NaOH and stirred for 0.5 h. The product was filtered off, washed with water and dried in a vacuum drying oven at 50° C. There were obtained 1.72 g of the title compound.

IR (in substance, $cm^{-1}$): 3424, 2925, 1593, 1510, 1439, 1377, 1234, 1188, 1160, 1109, 999, 935, 869, 803, 763, 720, 657, 613, 561.

CHN-elementary analysis: C, 45.43; H, 5.80; N, 14.12.
Fe-content: 10.68% [m/m]

Example 7

Tris-(5-chloro-4,6-dimethylpyrimidine-2-ol-1-oxide)-iron(III) complex

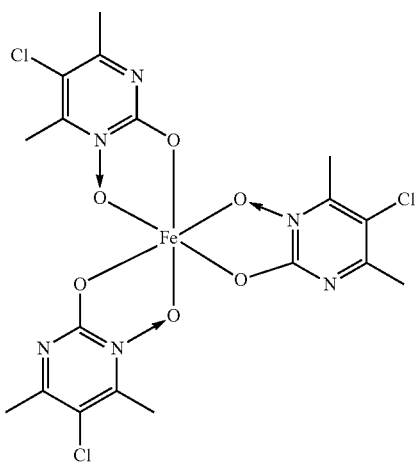

6.73 mmol (3.8 g, approximately 37% purity, 63% ammonium chloride) and 0.77 mmol (0.31 g, approximately 53% purity, 47% ammonium chloride) 5-chloro-4,6-dimethylpyrimidine-2-ol-1-oxide hydrochloride were dissolved in 25 ml of water and 2.5 mmol (0.68 g) $FeCl_3 \cdot 6H_2O$ dissolved in 2 ml water were added. The solution was adjusted to pH 5.96 with 14.8 ml 1 M NaOH and stirred for 0.5 h. The product was filtered off, washed with water and dried in a vacuum drying oven at 50° C. There was obtained 1.37 g of the title compound.

IR (in substance, $cm^{-1}$): 2929, 2363, 1688, 1589, 1509, 1431, 1390, 1375, 1196, 1169, 1092, 1016, 968, 847, 759, 694, 667, 553.

CHN-elementary analysis: C, 37.01; H, 2.83; N, 14.47.
Fe-content: 9.88% [m/m]

Example 8

Tris-(4-ethylpyrimidine-2-ol-1-oxide)-iron(III) complex

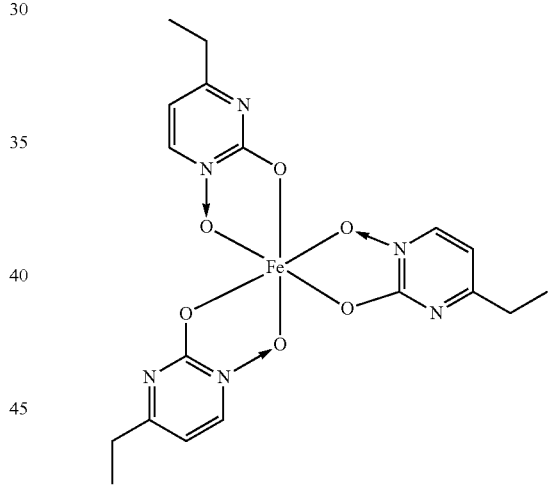

63 mmol (11.13 g) 4-ethylpyrimidine-2-ol-1-oxide hydrochloride were dissolved in 20 ml water and 21 mmol (5.68 g) $FeCl_3 \cdot 6H_2O$ dissolved in 5 ml water were added. The solution was adjusted to pH 6.17 with 125.6 ml 1 M NaOH and stirred for 0.5 h. The product was filtered off, washed with water and dried in a vacuum drying oven at 50° C. There was obtained 9.52 g of the title compound.

IR (in substance, $cm^{-1}$): 3083, 2974, 2936, 2876, 1596, 1543, 1511, 1460, 1428, 1313, 1249, 1194, 1143, 1107, 1079, 1056, 991, 948, 811, 770, 748, 696, 639, 598, 531, 502.

CHN-elementary analysis: C, 44.67; H, 4.52; N, 17.36.
Fe-content: 11.40% [m/m]

Example 9

Tris-(6-ethyl-4-methylpyrimidin-2-ol-1-oxide)-iron(III) complex

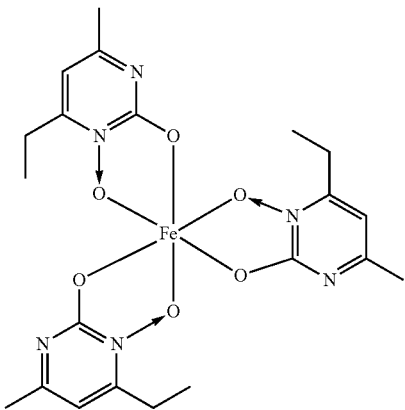

11.4 mmol (2.17 g) 6-ethyl-4-methylpyrimidine-2-ol-1-oxide hydrochlorid were dissolved in 5 ml water and 3.8 mmol (1.03 g) FeCl$_3$*6H$_2$O dissolved in 2 ml water were added. The solution was adjusted to pH 6.3 with 22.7 ml 1 M NaOH and stirred for 0.5 h. The product was filtered off, washed with water and dried in a vacuum drying oven at 50° C. There was obtained 1.89 g of the title compound.

IR (in substance, cm$^{-1}$): 3515, 3080, 2974, 2938, 1598, 1550, 1516, 1461, 1427, 1401, 1317, 1257, 1229, 1149, 1104, 1060, 1035, 985, 918, 851, 813, 768, 681, 651, 557, 522.

CHN-elementary analysis: C, 47.48; H, 5.44; N, 15.81.

Fe-content: 10.32% [m/m]

Chloride-content: 0.0% [m/m]

Example 10

Tris-(4-methyl-6,7-dihydro-5H-cyclopenta[d]pyrimidin-2-ol-1-oxide)-iron(III) complex

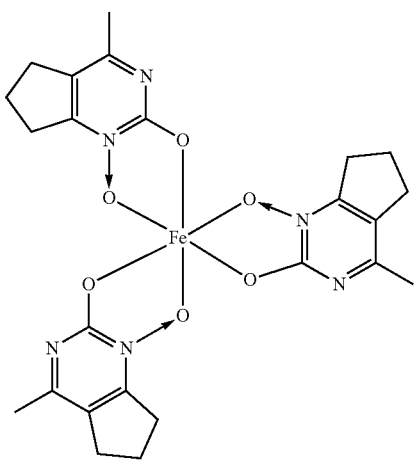

21 mmol (4.73 g) 4-methyl-6,7-dihydro-5H-cyclopenta[d]pyrimidine-2-ol-1-oxide hydrochlorid (content approximately 90%) were dissolved in 30 ml water and 7.0 mmol (1.89 g) FeCl$_3$*6H$_2$O dissolved in 5 ml water were added. The solution was adjusted to pH 5.96 with 41.6 ml 1 M NaOH and stirred for 0.5 h. The product was filtered off, washed with water and dried in a vacuum drying oven at 50° C. There was obtained 3.8 g of the title compound.

IR (in substance, cm$^{-1}$): 2918, 2361, 2326, 1599, 1571, 1499, 1429, 1382, 1359, 1311, 1279, 1232, 1208, 1173, 1100, 1067, 1043, 1013, 970, 945, 904, 881, 836, 761, 733, 663, 566, 528, 499.

CHN-elementary analysis: C, 50.36; H, 4.98; N, 14.88.

Fe-content: 9.71% [m/m]

Chloride-content: 1.05% [m/m]

Example 11

Tris-(4-methyl-5,6,7,8-tetrahydrochinazoline-2-ol-3-oxide)-iron(III) complex

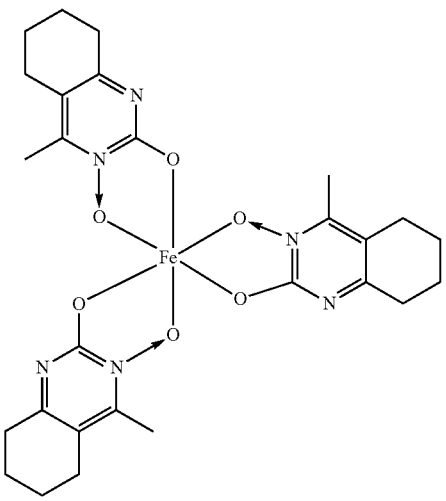

55 mmol (14.3 g) 4-methyl-5,6,7,8-tetrahydrochinazoline-2-ol-3-oxide hydrochloride were dissolved in 30 ml water and 18.3 mmol (4.95 g) FeCl$_3$*6H$_2$O dissolved in 5 ml water were added. The solution was adjusted to pH 6.19 with 110.7 ml 1 M NaOH and stirred for 0.5 h. The product was filtered off, washed with water and dried in a vacuum drying oven at 50° C. There was obtained 10.7 g of the title compound.

IR (in substance, cm$^{-1}$): 2932, 2859, 1586, 1510, 1446, 1421, 1377, 1348, 1308, 1267, 1229, 1189, 1168, 1100, 1079, 1057, 1030, 969, 889, 846, 824, 762, 704, 654, 614, 571, 507.

CHN-elementary analysis: C, 53.25; H, 5.49; N, 13.76.

Fe-content: 9.03% [m/m]

Chloride-content: 0.0% [m/m]

Example 12

Tris-(4-propane-2-yl)pyrimidine-2-ol-1-oxide)-iron(III) complex

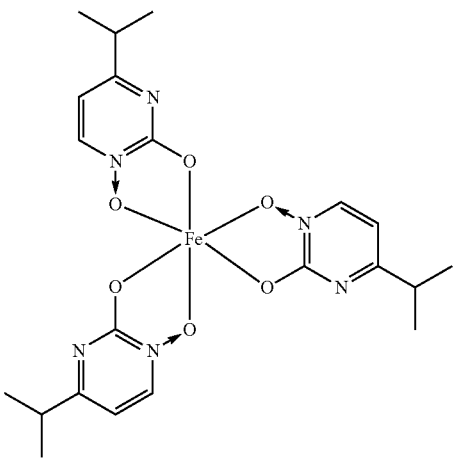

9.76 mmol (1.86 g) 4-(propane-2-yl)pyrimidine-2-ol-1-oxide hydrochlorid were dissolved in 5 ml water and 3.25 mmol (0.88 g) FeCl$_3$*6H$_2$O dissolved in 2 ml water were added. The solution was adjusted to pH 6.04 with 18.5 ml 1 M NaOH and stirred for 0.5 h. The product was filtered off, washed with water and dried in a vacuum drying oven at 50° C. There was obtained 1.64 g of the title compound.

IR (in substance, cm$^{-1}$): 3071, 2965, 2930, 2871, 1594, 1540, 1510, 1467, 1428, 1373, 1309, 1239, 1204, 1152, 1132, 1108, 1049, 970, 931, 881, 834, 809, 777, 733, 712, 645, 599, 552, 514.

CHN-elementary analysis: C, 47.53; H, 5.01; N, 15.84.
Fe-content: 10.86% [m/m] (ICP)
Chloride-content: 0.60% [m/m]

Example 13

Tris-(4-ethyl-6-methylpyrimidine-2-ol 1-oxide)-iron(III) complex

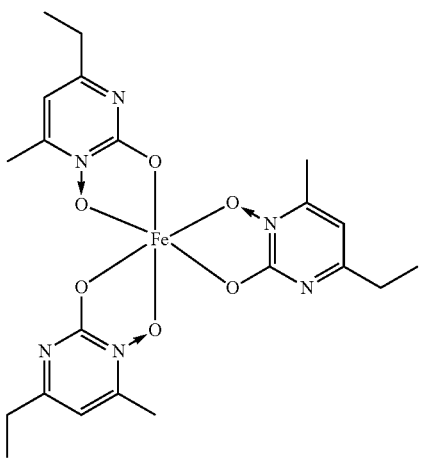

3.51 mmol (0.69 g) of 4-ethyl-6-methylpyrimidine-2-ol 1-oxide hydrochloride were dissolved in 3 ml water and 1.17 mmol (0,316 g) FeCl$_3$*6H$_2$O were added. The solution was adjusted to pH 6.37 with 6.975 ml of 1 M NaOH and stirred further for 0.5 h. The product was filtered off, washed with water and dried at 50° C. in a vacuum oven. This gave 0.63 g (92% Fe-yield) of the title compound.

IR (neat, cm$^{-1}$): 2970, 2936, 2876, 1750, 1685, 1601, 1552, 1511, 1462, 1441, 1404, 1386, 1362, 1308, 1231, 1196, 1154, 1106, 1056, 1034, 984, 846, 807, 790, 770.

CHN elemental analysis: C, 42.43; H, 5.43; N, 14.03.
Fe content: 9.5% [w/w]

Example 14

Tris-(5-ethyl-4,6-dimethylpyrimidine-2-ol 1-oxide)-iron(III) complex

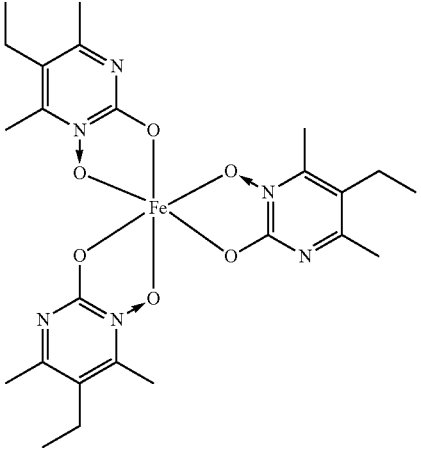

6.68 mmol (1.44 g) 5-ethyl-4,6-dimethylpyrimidine-2-ol 1-oxide hydrochloride (Yamaguchi et al., J. Inorg. Biochemistry 2006, 100, 260-269) and 2.23 mmol (0.485 g) of FeCl$_3$*6H$_2$O were dissolved in 7 ml of water. The solution was adjusted with 1 M NaOH to pH 6.0 and stirred for 0.5 h. The product was filtered off, washed with water and dried at 50° C. in a vacuum oven. This gave 0.98 g (75% Fe yield) of the title compound.

IR (neat, cm$^{-1}$): 2965, 1589, 1512, 1450, 1375, 1228, 1181, 1100, 1057, 1011, 958, 863, 768, 716, 685, 664.

CHN elemental analysis: C, 49.67; H, 5.83; N, 14.52.
Fe-content: 9.54% [w/w]
Chloride content: 0.0% [w/w]

Example 15

Tris-(4-tert-butylpyrimidine-2-ol 1-oxide)-iron(III) complex

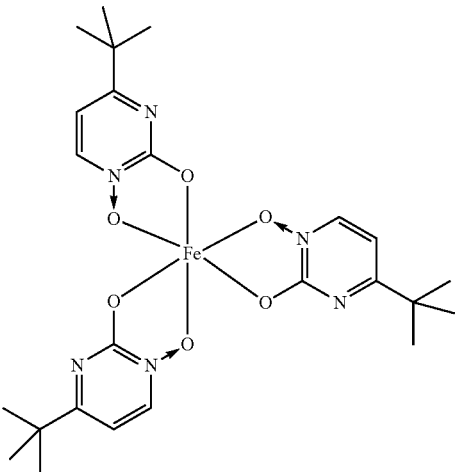

35.5 mmol (7.65 g) 4-tert-butylpyrimidine-2-ol 1-oxide hydrochloride were dissolved in 15 ml water and 11.84 mmol (3.20 g) FeCl$_3$*6H$_2$O were added. The suspension was adjusted to pH 6.1 with 69.4 ml of 1 M NaOH and stirred further for 0.5 h. The product was filtered off, washed with water and dried at 50° C. in a vacuum oven. This gave 6.44 g (99% Fe-yield) of the title compound.

IR (neat, cm$^{-1}$): 2965, 1598, 1535, 1506, 1477, 1419, 1364, 1339, 1273, 1238, 1217, 1159, 1122, 1025, 967, 829, 810, 779, 717, 701.

Fe content: 10.15% [w/w]
Chloride content: 0.65% [w/w]

Example 16

Tris-(5,6-dimethylpyrimidine-2-ol 1-oxide)-iron(III) complex

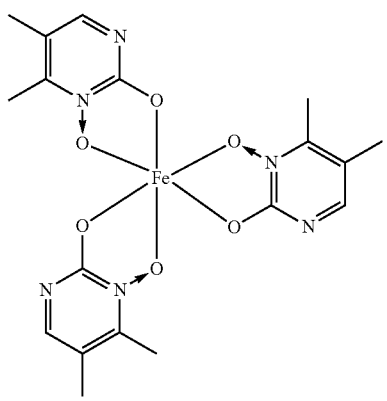

14.4 mmol (2.93 g) 5,6-dimethylpyrimidin-2-ol hydrochloride were dissolved in 20 ml water and 4.6 mmol FeCl$_3$ (0.76 g) dissolved in 10 ml of water were added. The solution was adjusted with 6.26 ml of 1 M NaOH to pH 5.8 and stirred for 0.5 h. The product was filtered off, washed with water and dried at 50° C. in a vacuum oven. This gave 2.22 g (92% Fe-yield) of the title compound.

IR (neat, cm$^{-1}$): 3409, 1613, 1518, 1443, 1403, 1361, 1241, 1221, 1202, 1177, 1094, 1007, 880, 762, 714.

CHN elemental analysis: C, 40.77; H, 4.95; N, 15.85.
Fe content: 10.68% [w/w]
Chloride content: 1.1% [w/w]

Example 17

Tris-(6-n-propylpyrimidine-2-ol 1-oxide)-iron(III) complex

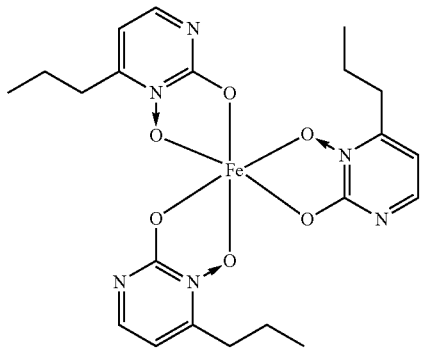

15 mmol (2.97 g) 6-n-propylpyrimidine-2-ol 1-oxide hydrochloride and 5 mmol (1.334 g) FeCl3*6H2O were dissolved in 42 ml water and 18 ml of ethanol and maintained at 50° C. 30% sodium hydroxide solution was added to pH 5.2 and the suspension was cooled to room temperature. The product was filtered off, washed with water and dried at 50° C. in a vacuum oven. This gave 2.2 g (85% Fe-yield) of the title compound.

IR (neat, cm$^{-1}$): 3072, 2961, 1594, 1541, 1507, 1460, 1426, 1380, 1337, 1246, 1141, 1108, 1088, 979, 870, 838, 799, 768, 733, 691.

Fe content: 10.74% [w/w]
Chloride content: 0.0% [w/w]

Example 18

Tris-(4-(ethylamino)pyrimidine-2-ol 1-oxide)-iron(III) complex

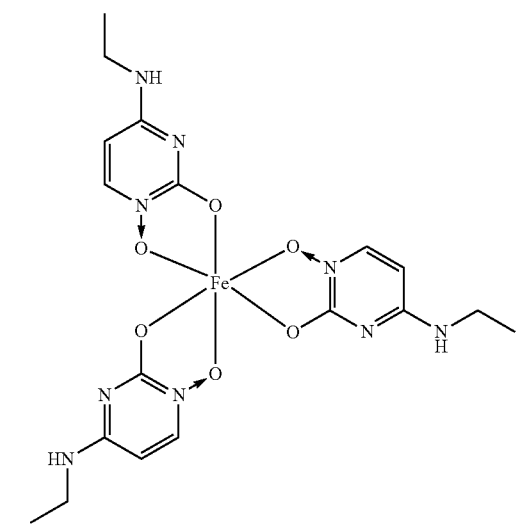

3 mmol (0.602 g) 4-(ethylamino)-pyrimidine-2-ol 1-oxide hydrochloride (Yamaguchi et al, J. Inorg Biochemistry 2006, 100, 260-269) were dissolved in 20 ml water, and 1 mmol (0.27 g) FeCl$_3$*6H$_2$O dissolved in 2 ml of water were added. The solution was adjusted with 1 M NaOH to pH 5.7 and stirred for another 15 min. The product was filtered off, washed with water and dried at 50° C. in a vacuum oven. This gave 0.43 g (85% Fe-yield) of the title compound.

IR (neat, cm$^{-1}$): 3287, 2975, 1620, 1588, 1531, 1490, 1448, 1381, 1344, 1283, 1254, 1178, 1156, 1096, 1066, 1014, 826, 784, 754, 708

Fe-content: 11.03% [w/w]
Chloride content: 0.47% [w/w]

Pharmacological Testing Method:

The excellent Fe utilizations that can be accomplished through the Fe complexes according to the invention were measured by means of the following mouse model.

Male NMRI (SPF) mice (approximately 3 weeks old) were fed a low-iron diet (approx. 5 ppm iron) for approximately 3 weeks. The iron complexes were then administered to them by means of a stomach tube (2 mg iron/kg body weight/day) for 2 times 5 days, with an interruption of 2 days (days 1-5 and 8-12). Utilization on day 15 was calculated from the hemoglobin increase and the body weight increase in accordance with the formula

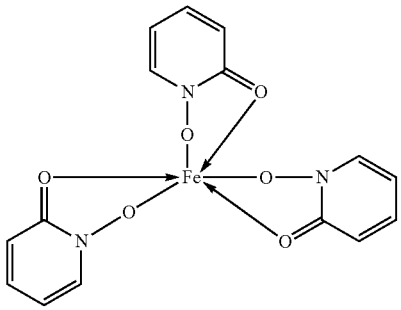

$$\text{Utilization (\%)} = \frac{\Delta \text{ iron utilization} * 100}{\text{Fe } Dos.}$$

$$= \frac{(\text{Fe } ut. - \text{Fe } ut. Control) * 100}{\text{Fe } Dos.}$$

$= [(Hb_{2(3)} \cdot BW_{9(14)} - Hb_1 * BW_4) * 0.07 * 0.0034 -$
$(Hb_{2(3)\ Control} * BW_{9(14)\ Control} - Hb_{1\ Control} * BW_{4\ Control}) *$
$0.07 * 0.0034)] * 100/\text{Fe } Dos.$ $= [(Hb_{2(3)} * BW_{9(14)} - Hb_1 * BW_4) * 0.000238 -$
$(Hb_{2(3)\ Control} * BW_{9(14)\ Control} - Hb_{1\ Control} * BW_{4\ Control}) *$
$0.000238] * 100/\text{Fe } Dos.$ $= (Hb_{2(3)} * BW_{9(14)} - Hb_1 * BW_4 - Hb_{2(3)\ Control} *$
$BW_{9(14)\ Control} + Hb_{1\ Control} * BW_{4\ Control}) *$
$0.0238/\text{Fe } Dos.$ 0.07=Factor for 70 ml blood per kg body weight (BW)
0.0034=Factor for 0.0034 g Fe/g Hb
$Hb_1$=Hemoglobin level (g/l) on day 1
$Hb_{2(3)}$=Hemoglobin level (g/l) on day 8 (or 15)
$BW_4$=body weight (g) on day 1
$BW_{9(14)}$=body weight (g) on day 8 (or 15)
$Hb_{1\ Control}$=average hemoglobin level (g/l) on day 1 in the control group,
$Hb_{2(3)\ Control}$=average hemoglobin level (g/l) on day 8 (or 15) in the control group,
$BW_{4\ Control}$=average body weight (g) on day 1 in the control group,
$BW_{9(14)\ Control}$=average body weight (g) on day 8 (or 15) in the control group,
Fe Dos.=entire administered iron (mg Fe) over 5 or 10 days,
Fe ut.=$(Hb_{2(3)}*BW_{9(14)}-Hb_1*BW_4)*0.07*0.0034$ (mg Fe)
Δ Utilization=Fe tot. utilized (examined group)–Fe ut. Control group, utilized from food, (mg Fe)

TABLE 1 iron utilizations:

| Example-No. | Utilization n 15 d (abs. %) |
|---|---|
| 1 | 89 |
| 2 | 80 |
| 3 | 74 |
| 4 | 76 |
| 5 | not determined |
| 6 | 70 |
| 7 | 64 |
| 8 | 82 |
| 9 | 69 |
| 10 | 70 |
| 11 | 74 |
| 12 | 55 |
| 16 | 57 |
| comparative example* | 25 |

*Comparative example:

As a comparative example the tris(pyridinone-2-ol-1-oxide)-iron(III) complex compound of the formula:

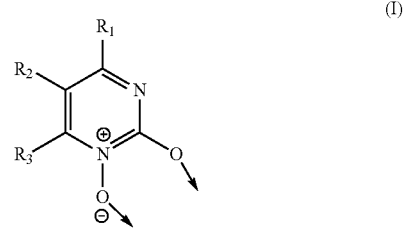

(III)

was prepared according to EP 0138420 and tested to demonstrate the influence of the heterocyclic base body. EP 0138420 discloses in example 7 only tris(pyridinon-2-ol-1-oxide)-iron (III) complex compounds which carry a further substituent on the pyridine ring. Unsubstituted tris(pyridinone-2-ol-1-oxide)-iron(III) complex compounds as used in the present comparative example are not disclosed therein. As can be seen from the results in the above-mentioned table the corresponding pyrimidine compound of example 1 according to the present invention exhibits significantly improved iron utilization compared to the comparative pyridine compound according to EP 0138420.

The invention claimed is:

1. A method for the treatment of iron deficiency diseases and iron deficiency anemias and the symptoms associated therewith, the method comprising administering to a patient in need thereof complex compounds or the pharmaceutically acceptable salts thereof which contain at least one ligand of the formula (I):

(I)

wherein
the arrows respectively represent a coordinate bond to one or different iron atoms, and
$R_1$, $R_2$, $R_3$ may be the same or different and are selected from the group consisting of:
hydrogen,
optionally substituted alkyl,
halogen,
optionally substituted alkoxy,
optionally substituted aryl,
optionally substituted alkoxycarbonyl,
optionally substituted amino, and
optionally substituted aminocarbonyl, or
$R_1$ and $R_2$ or $R_2$ and $R_3$ together with the carbon atoms to which they are bonded, form an optionally substituted saturated or unsaturated 5- or 6-membered ring, which may optionally contain one or more heteroatoms.

2. The method according to claim 1, wherein
$R_1$, $R_2$, $R_3$ may be the same or different and are selected from the group consisting of:

hydrogen,
optionally substituted alkyl,
halogen,
optionally substituted alkoxy,
optionally substituted aryl,
optionally substituted alkoxycarbonyl, and
optionally substituted aminocarbonyl, or $R_1$ and $R_2$ or $R_2$ and $R_3$ together with the carbon atoms to which they are bonded, form an optionally substituted saturated or unsaturated 5- or 6-membered ring, which may optionally contain one or more heteroatoms.

3. The method according to claim 1, wherein $R_1$, $R_2$, $R_3$ may be the same or different and are selected from the group consisting of:

hydrogen,
optionally substituted alkyl, and
halogen, or $R_1$ and $R_2$ or $R_2$ and $R_3$ together with the carbon atoms to which they are bonded form a 5- or 6-membered carbocyclic ring.

4. The method according to claim 1, wherein $R_1$, $R_2$, $R_3$ may be the same or different and are selected from the group consisting of hydrogen, alkyl which may optionally be substituted by alkoxy, and halogen, or $R_1$ and $R_2$ or $R_2$ and $R_3$ form together a propylene (—$CH_2$—$CH_2$—$CH_2$—), a butylene (—$CH_2$—$CH_2$—$CH_2$—$CH_2$—), azabutylene or oxabutylene group.

5. The method according to claim 1, wherein $R_1$, $R_2$, $R_3$ are identical or different and are selected from the group consisting of hydrogen and alkyl, with the proviso that at least one of the substituents $R_1$, $R_2$, and $R_3$ is alkyl.

6. The method according to claim 1, wherein $R_2$ is hydrogen, and $R_1$ and $R_3$ are each the same or different and are selected from alkyl.

7. The method according to claim 1, wherein the iron(III) complex compounds or the pharmaceutically acceptable salts thereof are of the formula:

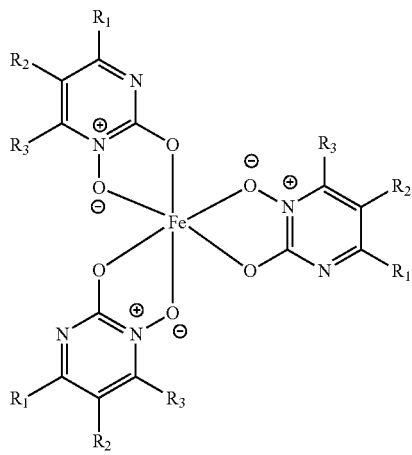

wherein $R_1$, $R_2$, $R_3$ may be the same or different and are defined as in claim 2.

8. The method according to claim 1, wherein the iron(III) complex compounds are in solid form.

9. The method according to claim 1, comprising administering the iron(III) complex compounds orally.

10. The method according to claim 1, comprising administering the iron(III) complex compounds in the form of a solid formulation, comprising pills, tablets, enteric-coated tablets, film tablets, layer tablets, sustained release formulations, depot formulations, dragees, suppositories, granulates, microcapsules, microformulations, nanoformulations, capsules, enteric-coated capsules and powders, or in the form of a liquid formulation including a drinkable formulation comprising a syrup, elixir, solution, suspension, and juice.

11. The method according to claim 1, comprising administering the iron(III) complex compounds in the form of a medicament, which further comprises at least one physiological compatible carrier or excipient.

12. The method according to claim 1, comprising administering the iron(III) complex compounds in combination with at least one further medicament which acts on the iron metabolism.

* * * * *